United States Patent [19]
Heintz et al.

[11] Patent Number: 6,130,090
[45] Date of Patent: Oct. 10, 2000

[54] METHODS OF PERFORMING GENE TRAPPING IN BACTERIAL AND BACTERIOPHAGE-DERIVED ARTIFICIAL CHROMOSOMES AND USE THEREOF

[75] Inventors: Nathaniel Heintz, Pelham Manor; Weining Jiang; Xiangdong W. Yang, both of New York, all of N.Y.

[73] Assignee: The Rockefeller University, New York, N.Y.

[21] Appl. No.: 09/007,206

[22] Filed: Jan. 14, 1998

Related U.S. Application Data

[63] Continuation-in-part of application No. 08/880,966, Jun. 23, 1997.

[51] Int. Cl.$^7$ ............................................. C12N 15/87
[52] U.S. Cl. ................ 435/466; 435/320.1; 435/440; 435/455; 435/463; 435/462; 435/471; 435/473; 435/476
[58] Field of Search .................... 435/320.1, 455, 435/463, 462, 466, 473, 440, 471, 476

[56] References Cited

FOREIGN PATENT DOCUMENTS

| 0742285 | 11/1996 | European Pat. Off. . |
| WO 97/29202 | 8/1997 | WIPO . |

OTHER PUBLICATIONS

Boren et al., Genome Research, 6:1123–30 (1996).
Chatterjee et al., Genetic Analysis 13:33–42 (1996).
Balasubramanian et al., *J. of Bacteriology* 178:273–279 (1996).
Birnboim et al., *Nucleic Acids Res.* 7:1513–1523 (1979.
Bochner et al., *J. Bacteriol.* 143:926–33 (1980).
Boyseu et al., *Genome Research,* 7:330–338 (1997).
Bradley et al., *Nature Genet.* 14:121–3 (1997).
Brinster et al. (1989) *Proc.Natl.Acad.Sci.* 86:7087–91.
Brinster et al., *Proc.Natl.Acad.Sci.* 85:836–840 (1988).
Burke et al., *Science* 236:806–12.
Clark et al., *Critical Reviews in Microbiology* 20:125–142 (1994).
Deng and Capecchi (*MCB,* 12:3365–3371).
Dillon et al., *Trends Genet.* 9:134–7 (1993).
Fujitani et al. (1995) Genetics 140:797–809.
Gnirke et al. (1993) Genomics 15:659–67.
Hamilton et al., *J. Bacteriol.* 171:4617–22 (1989).
Harrington et al. *Nature Genetics,* 15:345–355 (1977).
Hashimoto–Gotoh et al. (1977) J. Bacteriol. 131:405–12.
Hosoda et al., *Nucleic acids Res.* 18:3863–9 (1990).
Ioannou et al., *Nat. Genet.,* 6:84–89 (1994).
Jaenisch et al., *Science* 240:1468–74 (1985).
Joyner, A., Ed. *Gene Targeting, a practical approach,* IRL Press: Oxford, New York, Tokyo Only Table of contents Provided.
Kennison, *Trends Genet.* 9:75–9 (1993).
Kim et al. *MCB,* 12:363–3643 (1992).
Kim et al., *Proc.Natl.Acad.Sci.* 93:6297–6301 (1996).
Kuhn et al., *Science* 269:1427–9 (1995).
Maloy et al., *Bacteriol.* 145:1110 (1981).
McKee et al., *Chromosoma* 7:479–488 (1996).
Mejia et al., *Genome Res.,* 7:179–186 (1997).
Monaco et al., *Trends Biotechnol* 12:280–286 (1994).
O'Connor et al. *Science,* 244:1307–1312 (1989).
Palmiter et al., *Cell* 41:343–5 (1985).
Peakman et al., *Proc.Natl.Acad.Sci.* 93:10222–10227 (1996).
Peterson et al., TIG (*Trends Genet.*) 13:61–66 (1997).
Reiss et al., *Proc.Natl.Acad.Sci.* 93:3094–3098 (1996).
Shizuya et al., Proc. Natl. Acad. Sci. 89:8794–8797 (1992).
Spencer et al. (1993) Meth.: Comp. Meth. Enzymol. 5:161–75.
Tsien et al., *Cell* 87:1317–26 (1996).
Wang et al., *Genomics* 24:527–34 (1994).
Wilson et al., *Annu.Rev.Cell.Biol.* 6:679–714 (1990).
Woo et al., *Nucleic Acids Res.,* 22:4922–31 (1994).
Wooster et al., *Nature* 378:789–92 (1995).
Yang et al., *Development* 122:555–66 (1996).

*Primary Examiner*—Remy Yucel
*Attorney, Agent, or Firm*—Klauber & Jackson

[57] ABSTRACT

A method of efficiently sequencing multiple exons from complex genomic DNAs is disclosed. The methodology includes the use of bacterial and bacteriophage-derived artificial chromosomes (BBPACs) in novel gene trapping protocols. Targeted gene trapping by homologous recombination, and random gene trapping with the use of a transposon system are exemplified. Included in the invention are methods of preparing a gene map from BBPAC contigs, the resulting gene maps, methods of constructing a cDNA library from BBPAC contigs, and the resulting cDNA libraries.

30 Claims, 3 Drawing Sheets

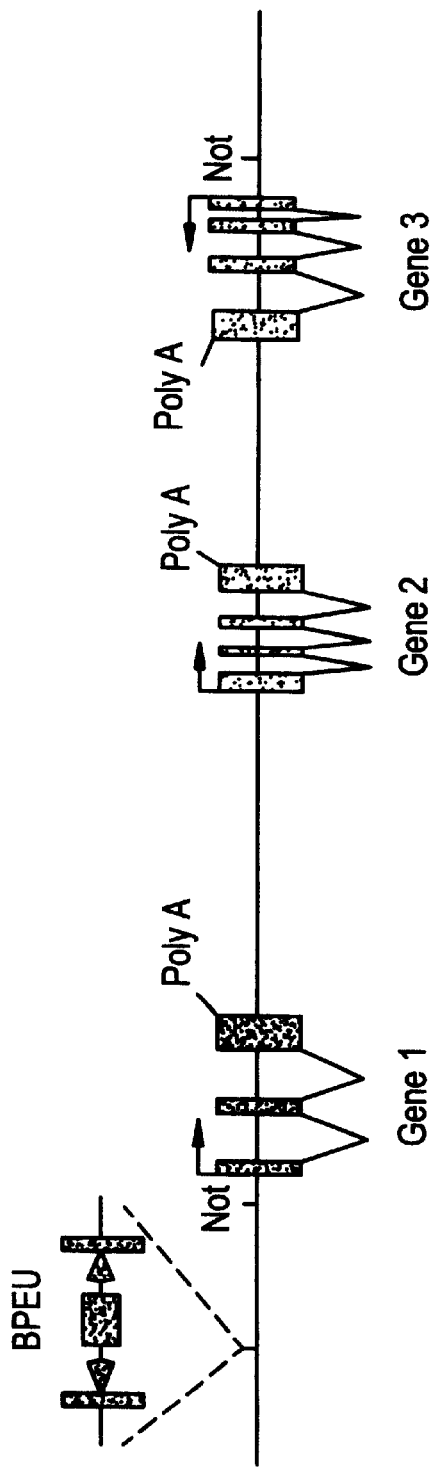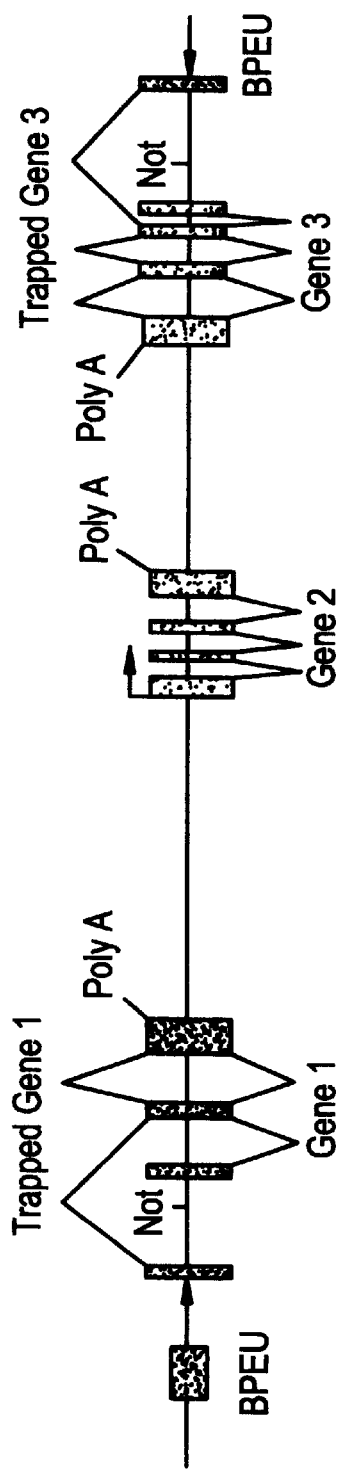

METHODS OF PERFORMING GENE TRAPPING IN BACTERIAL AND BACTERIOPHAGE-DERIVED ARTIFICIAL CHROMOSOMES AND USE THEREOF

CROSS-REFERENCE TO RELATED APPLICATIONS

The present Application is a Continuation-In-Part of copending U.S. Ser. No. 08/880,966, filed Jun. 23, 1997, the disclosure of which is hereby incorporated by reference in its entirety. Applicants claim the benefits of this Application under 35 U.S.C. § 120.

GOVERNMENTAL SUPPORT

The research leading to the present invention was supported, at least in part, by a grant from the National Science Foundation Grant No. MCB-9316625. Accordingly, the Government may have certain rights in the invention.

FIELD OF THE INVENTION

This invention relates generally to methods of efficiently isolating coding sequences from complex genomic DNAs. More particularly, the present invention relates to a novel methodology for gene trapping in bacterial and bacteriophage-derived artificial chromosomes. The procedures are exemplified by either targeted gene trapping using homologous recombination methodology or random gene trapping employing a transposon system. Included in the invention are methods of preparing a gene map from a bacterial or bacteriophage-derived artificial chromosome contig, the resulting gene maps, methods of constructing a cDNA library from bacterial or bacteriophage-derived artificial chromosomes contigs, and the resulting cDNA libraries.

BACKGROUND OF THE INVENTION

In recent years, the sequencing of the genomes of individual species, including humans, has become a major goal of biomedical research. The most prevalent procedure for sequencing the coding regions of a gene relies on RNA based methods, such as direct screening of a cDNA library. However, such methods are inherently biased towards the identification of nucleic acids which are prevalent in the tissue sample being studied. Therefore, genes which are expressed solely in tissues that are difficult to obtain, and/or expressed under relatively rare circumstances, have a good chance of being missed. Particularly in the latter case, these genes are likely to play a unique role during a specific cellular challenge, and thus could be important in a specific diseased state.

Exon trapping is one method of potentially overcoming the inherent bias of the mRNA based procedures of genomic sequencing. Exon trapping was originally developed to efficiently isolate coding sequences from complex genomic sequences [Duyk et al., *PNAS* 87, 8995–8999 (1990); Buckler et al., *PNAS* 88:4005–4009 (1991)]. This method is based on the selection of exons which are flanked by functional 5' and 3' splice sites. Conventional exon trapping vectors contain a driving promoter (i.e. SV40 promoter, metallothionein-1 promoter) which controls the expression of an exon having a 5' splice site; an intron with multiple cloning sites; and a 3' exon having a 3' splice site and a polyadenylation (poly A) signal sequence. Genomic fragments containing potential exons are first subcloned into the intron. The resulting plasmid DNA is then transfected into COS-7 cells, which transcribe and then process the RNA products. The mature RNAs containing the trapped exons can be amplified by reverse transcriptase PCR and subcloned. The trapped exons can be identified by sequencing the cloned cDNA products. In addition to its simplicity and efficiency, exon trapping is also independent of the amount, location, and timing of the expression of a given gene, and therefore is preferable to mRNA based methods. Consequently, exon trapping has become widely employed in transcription map construction for positional cloning and in general genomic sequencing.

Unfortunately, current exon trapping systems have a number of limitations. First, the size of the genomic insert in the exon-trapping vector is limited to 1–2 kilobases (kb), so the resulting trapped exon is usually a single small exon (80–150 basepairs (bp)). Such small exons are usually difficult to use in subsequent biological procedures, such as library screening, Northern blot analysis, or in in situ hybridizations. Second, different exons from a single gene will be dispersed in different trapping vectors. Therefore, reconstruction of the gene from the small pieces of the gene requires considerable additional work. Third, subcloning of small genomic fragments may disrupt the elements necessary for proper splicing, thereby increasing the chance of missing certain exons. Fourth, current exon trapping systems can only be used in combination with specific cell lines (i.e. COS cells), since they require specific cellular factors to support the SV40 origin of replication, and as a result certain exons are spliced in a tissue specific manner, and therefore would be missed in the COS cells.

One recent advance towards solving some of these problems uses cosmid-based exon trapping vectors [Datson et al., *NAR* 24, 1105–1111 (1996)]. A specially designed cosmid vector is used, with a promoter and 5' splice site on one end, and 3' splice site and poly-adenylation signal sequence on the other end. The genomic insert now can be as large as 40 kb. In this case, multiple exons can be trapped together. Such a trapped gene segment can be greater than 800 bp. The major disadvantage of this system is that it is necessary to use a specialized genomic cosmid library. Furthermore, cosmid clones are inherently unstable.

An alternative to using a cosmid based system is to use one or more of the *E. coli* based cloning systems based on the *E. coli* fertility factor which have been developed to construct large genomic DNA insert libraries. These are bacterial artificial chromosomes (BACs) and P-I derived artificial chromosomes (PACs) [Mejia et al., *Genome Res.* 7:179–186 (1997); Shizuya et al., Proc. Natl. Acad. Sci. 89:8794–8797 (1992);Ioannou et al., *Nat. Genet.,* 6:84–89 (1994); Hosoda et al., *Nucleic Acids Res.* 18:3863 (1990)]. BACs are based on the *E. coli* fertility plasmid (F factor); and PACs are based on the bacteriophage P1. The size of DNA fragments from eukaryotic genomes that can be stably cloned in *Escherichia coli* as plasmid molecules has been expanded by the advent of PACs and BACs. These vectors propagate at a very low copy number (1–2 per cell) enabling genomic inserts up to 700 kb in size to be stably maintained in recombination deficient hosts. The host cell is required to be recombination deficient to ensure that non-specific and potentially deleterious recombination events are kept to a very minimum. As a result, libraries of PACs and BACs are relatively free of the high proportion of chimeric or rearranged clones typical in Yeast artificial chromosomes (YACs). [Burke et al., *Science* 236:806; Peterson et al., *Trends Genet.* 13:61 (1997); Choi, et al., *Nat. Genet.,* 4:117–223 (1993), Davies, et al., *Biotechnology* 11:911–914 (1993), Matsuura, et al., *Hum. Mol. Genet.,* 5:451–459

(1996), Peterson et al., *Proc. Natl. Acad. Sci.,* 93:6605–6609 (1996); Schedl, et al., *Cell,* 86:71–82 (1996); Monaco et al., *Trends Biotechnol* 12:280–286 (1994); Boyseu et al., *Genome Research,* 7:330–338 (1997)]. In addition, isolating and sequencing DNA from PACs or BACs involves simpler procedures than for YACs, and PACs and BACs have a higher cloning efficiency than YACs [Shizuya et al., Proc. Natl. Acad. Sci. 89:8794–8797 (1992);Ioannou et al., *Nat. Genet.,* 6:84–89 (1994); Hosoda et al., *Nucleic Acids Res.* 18:3863 (1990)]. Such advantages have made BACs and PACs important tools for physical mapping in many genomes [Woo et al., *Nucleic Acids Res.,* 22:4922 (1994); Kim et al., *Proc.Natl.Acad.Sci.* 93:6297–6301 (1996); Wang et al., *Genomics* 24:527 (1994); Wooster et al., *Nature* 378:789 (1995)]. Furthermore, the PACs and BACs are circular DNA molecules that are readily isolated from the host genomic background by classical alkaline lysis [Birnboim et al., Nucleic Acids Res. 7:1513–1523 (1979)]. In addition, BACs have been found to be an important source of genomic DNA for the direct sequencing of the human genome [Rowen et al., *Sequence* 278: 605–607 (1997)]. On the other hand, their use in gene identification is still extremely limited. Indeed, heretofore, BACs and PACs have not been shown to be useful in methods that directly isolate genes, such as exon trapping.

Therefore, there is a need to efficiently sequence coding regions of eukaryotic genes, and in particular human genes, which are expressed relatively rarely and/or only at specific times (such as the genes involved in circadian rhythms or those involved in body weight homeostasis); and/or are predominantly expressed in tissues that are difficult to obtain, such as the human organ of Corti. In addition there is a need to produce new and improved gene maps for BAC or PAC contigs. Furthermore, there is a need to compile new cDNA libraries that are not biased by the expression pattern of the tissue that serve as the source for the mRNAs used to construct the cDNA library.

The citation of any reference herein should not be construed as an admission that such reference is available as "Prior Art" to the instant application.

SUMMARY OF THE INVENTION

The present invention provides a novel and efficient method of determining the nucleotide sequence of a portion of a eukaryotic gene that minimally contains one exon which has a 3' splice acceptor, i.e., any exon other than the first exon. Preferably the portion of the eukaryotic gene contains two or more exons that have 3' splice acceptors. In a more preferred embodiment, the portion of the eukaryotic gene contains three or more exons that have 3' splice acceptors. In the most preferred embodiment, the portion of the eukaryotic gene contains all of the exons of the gene except the first exon.

The present invention includes methods of including a eukaryotic promoter exon/intron unit (PEU) in a Bacterial or Bacteriophage-Derived Artificial Chromosome (BBPAC) with a trappable eukaryotic gene. In one aspect of the present invention, the PEU is placed into existing BBPACs. Preferably the PEU is inserted operatively upstream to one or more exons of the trappable eukaryotic gene. More preferably, the PEU is inserted operatively upstream to all, or all but the first exon of the trappable eukaryotic gene.

In an alternative aspect of the present invention, BBPACs are constructed using vectors containing one or more PEUs, and genomic DNA containing trappable eukaryotic genes is inserted into the vectors to form a BBPAC containing one or more PEUs and trappable eukaryotic genes. Preferably a PEU is operatively upstream to one or more exons of the inserted trappable eukaryotic gene. More preferably, the PEU is operatively upstream to all but the first exon of the inserted trappable eukaryotic gene.

In one embodiment the trappable eukaryotic gene(s) are vertebrate genes. In a preferred embodiment of this type the vertebrate genes are mammalian genes. In a more preferred embodiment of this type the mammalian genes are human genes. In another embodiment the trappable eukaryotic gene(s) are invertebrate genes. In a preferred embodiment of this type the invertebrate genes are insect genes. In still another embodiment the trappable eukaryotic genes are plant genes.

In a related aspect, the present invention provides methods of obtaining a cell that contains a BBPAC containing a PEU and a trappable eukaryotic gene. Preferably the PEU is operatively upstream to one or more exons of the trappable eukaryotic gene. More preferably, the PEU is operatively upstream to all but the first exon of the trappable eukaryotic gene.

The present invention also includes methods of transcribing a trappable eukaryotic gene contained in a BBPAC in a eukaryotic cell. In one such embodiment the eukaryotic cell is a vertebrate cell. In a preferred embodiment of this type the vertebrate cell is a mammalian cell. In a more preferred embodiment the mammalian cell is a human cell. In another embodiment the eukaryotic cell is an invertebrate cell. In a preferred embodiment of this type the invertebrate cell is an insect cell. In still another embodiment the eukaryotic cell is a plant cell.

The present invention further provides methods of determining the nucleotide sequence of a trappable eukaryotic gene contained in a BBPAC. In another aspect, the present invention provides methods of preparing a gene map for a BBPAC contig. Still another aspect of the present invention includes methods of constructing a cDNA library from genomic DNA contained in a BBPAC genomic library. In a preferred embodiment the BBPAC either contains all of the exons of the eukaryotic gene, or alternatively, all of the exons of the gene except the first exon. In another preferred embodiment the BBPAC is a BAC.

The PEU of the present invention is specifically constructed to contain at least one 5' vector-derived exon and at least part of one intron (e.g., a fragment of an intron). In one such embodiment, the PEU does not contain a 3' polyadenylation sequence. In a preferred embodiment the PEU is a bi-directional eukaryotic promoter-exon/intron unit (BPEU).

The PEU of the present invention can be introduced into a host cell containing the BBPAC via a shuttle vector. In a preferred embodiment the shuttle vector is a conditional replication shuttle vector. The conditional replication shuttle vector is preferably a temperature sensitive shuttle vector (TSSV) having a temperature-sensitive origin of replication, such that the TSSV replicates at a permissive temperature, but does not replicate at a non-permissive temperature. In a particular embodiment, the permissive temperature is 30° C., and the non-permissive temperature is 43° C. The TSSV is diluted out when the host cell containing the TSSV is grown at the non-permissive temperature.

One aspect of the present invention relates to a method for placing a PEU operatively upstream to an exon of a trappable eukaryotic gene of a BBPAC. One such embodiment comprises introducing a conditional replication shuttle vector into a host cell under conditions in which the conditional replication shuttle vector can replicate and transform the host cell. The host cell comprises a BBPAC that contains a trappable eukaryotic gene, BBPAC vector DNA, and a second marker gene. The conditional replication shuttle vector comprises a first marker gene and the PEU. The PEU comprises a eukaryotic promoter, at least one 5' vector-derived exon, and at least one intron or fragment thereof. A 5' vector- derived exon is adjacent to the intron or fragment thereof and is operatively downstream from the eukaryotic promoter. The PEU and the first marker gene are configured on the conditional replication shuttle vector such that when the PEU is transferred from the conditional replication shuttle vector to the BBPAC, the first marker gene remains with the conditional replication shuttle vector. In a related embodiment of this type the PEU further comprises a third marker gene and/or the first marker gene can be counter-selected against. In a preferred embodiment, the first marker gene is a tetracycline resistance gene that can be counter-selected against by growing the cell in the presence of fusaric acid.

The transformed host cell is then grown under conditions in which the conditional replication shuttle vector can replicate, and under conditions that select for a cell that contains the first and second marker gene. The PEU is then transferred from the conditional replication shuttle vector to the BBPAC of the selected cell, while the first marker gene remains with the conditional replication shuttle vector. When the BBPAC contains a trappable eukaryotic gene, the PEU can integrate into the BBPAC and place one or more exons of the trappable eukaryotic gene operatively downstream of the PEU. (Of course, the presence of the trappable eukaryotic gene in the BBPAC is not required for the insertion of the PEU into the BBPAC, since the PEU can integrate into a BBPAC which does not contain a trappable gene.)

In a preferred embodiment of this type the PEU is transferred from the conditional replication shuttle vector to the BBPAC through homologous recombination between the conditional replication shuttle vector and the BBPAC.

In an alternative embodiment, the PEU is transferred from the conditional replication shuttle vector to the BBPAC by the addition of transposase to the host cell. In this case the PEU is positioned in between a pair of inverted transposon ends on the conditional replication shuttle vector. In one embodiment of this type, the host cell contains a nucleic acid encoding transposase; in another embodiment the BBPAC contains a nucleic acid encoding transposase; in still a third such embodiment the conditional replication shuttle vector contains a nucleic acid encoding transposase. In this case, the transposase remains with the conditional replication shuttle vector when the PEU is transferred. In all of these alternative embodiments, the transcription of the nucleic acid encoding transposase can be placed under the control of an inducible promoter and in such cases, the addition of transposase to the host cell is achieved by adding an inducer of the inducible promoter to the host cell. This facilitates the transcription of an mRNA encoding transposase which can then be translated by the host cell, resulting in the expression of transposase.

The present invention also includes methods of isolating a cell that contains a BBPAC with a trappable eukaryotic gene and a PEU. Preferably the PEU is operatively upstream of one or more exons of the trappable eukaryotic gene. One such embodiment comprises growing the cell under conditions in which the conditional replication shuttle vector cannot replicate, and in which a cell that contains the second and third marker genes is selected for, while a cell that contains the first marker gene is selected against. A cell containing a BBPAC having a PEU is then isolated. In this manner cells containing a PEU operatively upstream of one or more exons of a trappable eukaryotic gene can be obtained. In such an embodiment the PEU can further comprise the third marker gene and the first marker gene can be counter-selected against.

The present invention also includes a method of transcribing one or more exons of a trappable eukaryotic gene contained in a BBPAC in a eukaryotic cell. One such embodiment comprises isolating a BBPAC containing the trappable eukaryotic gene operably downstream of the PEU from an isolated cell that comprises the BBPAC. The isolated BBPAC is transfected into a eukaryotic cell and the eukaryotic cell is cultured. In this case the eukaryotic promoter of the PEU facilitates the transcription of the trappable eukaryotic gene into an mRNA. In a related embodiment the mRNA is used as a template for preparing a cognate cDNA in order to determine the nucleotide sequence of the trappable eukaryotic gene contained in the BBPAC by determining the nucleotide sequence of the cognate cDNA.

The present invention further provides additional methods of placing a PEU operatively upstream to a trappable eukaryotic gene contained in a BBPAC. One such embodiment comprises introducing a conditional replication shuttle vector into a host cell that contains the BBPAC under conditions in which the conditional replication shuttle vector can replicate and transform the host cell. The BBPAC contains a trappable eukaryotic gene, BBPAC vector DNA, and a second marker gene. The conditional replication shuttle vector contains a first marker gene, and a recombination cassette. The recombination cassette comprises a PEU flanked on both its 5' and 3' ends by nucleotide sequences that are homologous to BBPAC vector DNA and the recombination cassette, and the first marker gene are linked together on the conditional replication shuttle vector such that when the PEU integrates into the BBPAC, the first marker gene does not remain linked to the integrated PEU. The PEU comprises a eukaryotic promoter, at least one 5' vector-derived exon, and at least one intron or fragment thereof. In a preferred embodiment the PEU does not contain an exon encoding a 3' polyadenylation sequence. The 5' vector-derived exon is adjacent to the intron or fragment thereof and operatively downstream from the eukaryotic promoter. Thus when the BBPAC contains a trappable eukaryotic gene, the PEU can integrate into the BBPAC placing the exon of the trappable eukaryotic gene operatively downstream of the PEU. In a related embodiment of this type the PEU further comprises a third marker gene and/or the first marker gene can be counter-selected against. In a preferred embodiment of this type the first marker gene is a tetracycline resistance gene that can be counter-selected against by growing the cell in the presence of fusaric acid.

The transformed host cell is grown under conditions in which the conditional replication shuttle vector can replicate, and a cell that contains the first and second marker genes can be selected for. In this case a first homologous recombination event is allowed to occur between the recombination cassette and the BBPAC to form a co-integrate. The cell is then grown under conditions in which the conditional replication shuttle vector cannot replicate and in which a cell that contains the first and second markers is selected for. A cell containing the co-integrate between the recombination cassette and the BBPAC is thus selected for. This cell is then grown under conditions in which the conditional replication shuttle vector cannot replicate and in which a cell that contains the second marker gene is selected for. A second homologous recombination event is then allowed to occur between the conditional replication shuttle vector and the BBPAC. The PEU is thus allowed to integrate into the BBPAC and place the exon of the trappable eukaryotic gene operatively downstream of the PEU. In one such embodiment the eukaryotic promoter is a mammalian promoter and/or the eukaryotic gene is a mammalian gene. In another such embodiment the eukaryotic promoter is a plant promoter, and the eukaryotic gene is a plant gene.

A cell containing BBPAC having the integrated PEU can be isolated in a related embodiment. Such an embodiment comprises growing the cell under conditions in which a cell that contains the second and third marker genes is selected for, while a cell that contains the first marker gene is selected against. The cell containing the BBPAC having the PEU is then isolated. In this embodiment the PEU further comprises the third marker gene, and the first marker gene can be counter-selected against.

A particular embodiment of the present invention further includes a method of transcribing one or more exons of the trappable eukaryotic gene contained in a BBPAC in a eukaryotic cell. This embodiment comprises isolating the BBPACs containing the PEU from the isolated cell, and then transfecting the isolated BBPACs into eukaryotic cells. The eukaryotic cell are then cultured. When the PEU is operatively upstream of an exon (or more than one exon) of the trappable eukaryotic gene, the eukaryotic promoter of the PEU facilitates the transcription of the exon(s) of the trappable eukaryotic gene into an mRNA.

A related aspect of the present invention includes a method of determining the nucleotide sequence of the exon(s) of the trappable eukaryotic gene contained in the BBPAC. One such embodiment comprises preparing cognate cDNA by using the mRNA as a template, and determining the nucleotide sequence of the cognate cDNA. The nucleotide sequence of the exons of the trappable eukaryotic gene contained in the BBPAC is thus determined.

A preferred embodiment for a method for placing a PEU into a BBPAC containing a trappable eukaryotic gene comprises introducing a conditional replication shuttle vector into a host cell containing the BBPAC under conditions in which the conditional replication shuttle vector can replicate and transform the host cell. The BBPAC contains a trappable eukaryotic gene, BBPAC vector DNA, and a second marker gene; the conditional replication shuttle vector contains a RecA-like protein gene, a first marker gene, and a recombination cassette. The recombination cassette comprises a PEU flanked on both its 5' and 3' ends by nucleotide sequences that are homologous to BBPAC vector DNA. The recombination cassette, the RecA-like protein gene, and the first marker gene are linked together on the conditional replication vector such that when the PEU integrates into the BBPAC, the RecA-like protein gene and the first marker gene remain linked together, but neither the RecA-like protein gene nor the first marker gene remain linked to the integrated PEU. The PEU comprises a eukaryotic promoter, at least one 5' vector-derived exon, and at least one intron or fragment thereof. In a more preferred embodiment of this type the PEU does not contain an exon encoding a 3' polyadenylation sequence. The 5' vector-derived exon is adjacent to the intron or fragment thereof, and operatively downstream from the eukaryotic promoter. When the trappable eukaryotic gene comprises an exon with a 3' splice acceptor, the PEU can integrate into the BBPAC and place the exon of the trappable eukaryotic gene operatively downstream of the PEU. In a preferred embodiment of this type neither the host cell nor the BBPAC independently or in conjunction can support homologous recombination, without the conditional replication shuttle vector. The transformed host cell can be grown under conditions in which the conditional replication shuttle vector can replicate, the RecA-like gene can be expressed, and in which a cell that contains the first and second marker genes is selected for, and in which a first homologous recombination event is allowed to occur between the recombination cassette and the BBPAC to form a co-integrate. This cell is then grown under conditions in which the conditional replication shuttle vector cannot replicate and in which a cell that contains the first and second marker is selected for. In this way, a cell containing the co-integrate between the recombination cassette and the BBPAC is selected for. This cell is then grown under conditions in which the conditional replication shuttle vector cannot replicate and in which a cell that contains the second marker gene is selected for and wherein a second homologous recombination event is allowed to occur between the conditional replication shuttle vector and the BBPAC. The PEU can thus integrate into the BBPAC placing the exon of the trappable eukaryotic gene operatively downstream of the PEU.

In an alternative embodiment of this type, the PEU further comprises a third marker gene and/or the first marker gene can be counter-selected against. In a preferred embodiment of this type the first marker gene is a tetracycline resistance gene that can be counter-selected against by growing the cell in the presence of fusaric acid.

A related aspect of the invention further comprises a method of isolating such a cell which contains a BBPAC having a PEU. One such embodiment comprises growing the cell under conditions in which a cell that contains the second and third marker genes is selected for, while a cell that contains the first marker gene is selected against. A cell containing a BBPAC having a eukaryotic promoter exon/intron unit (PEU) is obtained. In one such embodiment the PEU further comprises the third marker gene, and the first marker gene can be counter-selected against.

A further related aspect of the present invention comprises a method of transcribing a trappable eukaryotic gene contained in a BBPAC in a eukaryotic cell. One such embodiment comprises isolating the BBPAC containing the PEU from the isolated cell and transfecting the isolated BBPAC into the eukaryotic cell. The eukaryotic cell is then cultured. When the PEU is operatively upstream of an exon (or more than one exon) of the trappable eukaryotic gene, the eukaryotic promoter of the PEU facilitates the transcription of the exon(s) of the trappable eukaryotic gene into an MRNA.

A related embodiment further includes a method of determining the nucleotide sequence of the exon(s) of the trappable eukaryotic gene contained in the BBPAC comprising preparing a cognate cDNA using the MRNA as a template and then determining the nucleotide sequence of the cognate cDNA. The nucleotide sequence of the trappable eukaryotic gene contained in the BBPAC is thus determined. In a preferred embodiment of this type preparation of the cognate cDNA is performed by PCR.

As is true for the entire invention, in this aspect of the invention, preferably the PEU is a bi-directional eukaryotic promoter-exon/intron unit (BPEU). Similarly it is preferred that the conditional replication shuttle vector is a temperature sensitive shuttle vector (TSSV) having a temperature-sensitive origin of replication, such that the TSSV replicates at a permissive temperature, but does not replicate at a non-permissive temperature. In another preferred embodiment the BBPAC is a BAC. In one particular embodiment the PEU comprises two 5' vector-derived exons and one intron or fragment thereof. In a preferred embodiment the two 5' vector-derived exons consist of the first exon of beta-globin and a fusion exon containing the second exon of beta-globin fused to the HIV-tat exon, and the intron is the HIV-tat intron or fragment thereof. In this embodiment the fusion exon is adjacent to the HIV-tat intron.

Another variation of the present invention includes a method of placing a eukaryotic promoter exon/intron unit (PEU) into a BBPAC by introducing a conditional replication shuttle vector into a host cell containing the BBPAC under conditions in which the conditional replication shuttle vector can replicate and transform the host cell. The BBPAC contains a trappable eukaryotic gene, BBPAC vector DNA, and a second marker gene, whereas the conditional replication shuttle vector comprises a first marker gene, the PEU, a mini-transposon containing a pair of inverted transposon ends, a nucleic acid encoding transposase, and an inducible promoter. The expression of transposase is maintained under the control of the inducible promoter. The PEU is positioned in between the pair of inverted transposon ends and the nucleic acid encoding transposase, the inducible promoter, and the first marker gene are positioned outside of the pair of inverted transposon ends. The PEU comprises a eukaryotic promoter, at least one 5' vector-derived exon, and at least one intron or fragment thereof. Preferably the PEU does not contain an exon encoding a 3' polyadenylation sequence. A 5' vector-derived exon is adjacent to the intron or fragment thereof and operatively downstream from the eukaryotic promoter. When the trappable eukaryotic gene comprises an exon with a 3' splice acceptor, the PEU can integrate into the BBPAC and place the exon of the trappable eukaryotic gene operatively downstream of the PEU. The transformed host cell is grown under conditions in which the conditional replication shuttle vector can replicate, and in which a cell that contains the first and second marker gene are selected for. The inducible promoter of this cell is induced and transposase is expressed. The PEU can then integrate into the BBPAC and place the exon of the trappable eukaryotic gene operatively downstream of the PEU. A cell that contains the first and second marker gene is then selected for. In a related embodiment of this type the PEU further comprises a third marker gene and/or the first marker gene can be counter-selected against. In a preferred embodiment of this type, the first marker gene is a tetracycline resistance gene that can be counter-selected against by growing the cell in the presence of fusaric acid.

A related embodiment further includes a method of isolating the cell containing the BBPAC having the PEU which comprises growing the cell under conditions in which the conditional replication shuttle vector cannot replicate, and in which a cell that contains the second and third marker genes are selected for, while a cell that contains the first marker gene is selected against. In a preferred embodiment of this type, the selection for the second and third marker genes are performed in one step, and the counterselection for the first marker gene is performed in a subsequent step. In either case a cell containing a BBPAC having a eukaryotic promoter exon/intron unit PEU is isolated. In this embodiment the PEU further comprises the third marker gene, and the first marker gene can be counter-selected against.

In a particular embodiment of this type the inducible promoter is the P-galactosidase promoter and the bacterial host expresses lacI$^q$. In a related embodiment the conditional replication shuttle vector encodes lacI$^q$. In either case the inducing of the inducible promoter comprises contacting the bacterial host cell with IPTG. In a preferred embodiment the amount of IPTG used to contact the bacterial host is controlled so that the BBPAC receives only a single transposon or none at all.

The conditional replication shuttle vector is preferably a temperature sensitive shuttle vector (TSSV) having a temperature-sensitive origin of replication, such that the TSSV replicates at a permissive temperature, but does not replicate at a non-permissive temperature. The BBPAC is preferably a BAC. The first marker gene is preferably a tetracycline resistance gene that can be counter-selected against by growing the cell in the presence of fusaric acid. In a more preferred embodiment the PEU is a bi-directional eukaryotic promoter-exon/intron unit (BPEU).

This aspect of the invention also provides for isolating a BBPAC which has a PEU from a cell containing the BBPAC. As any person having skill in the art would readily recognize once a PEU is introduced into a BBPAC, the subsequent isolation and manipulation of the BBPAC is independent of the method for placing the PEU into the BBPAC.

One specific embodiment comprises performing an alkaline lysis of the isolated cell therein isolating the BBPAC DNA. The isolated BBPAC DNA is next electroporated into competent bacterial cells, and then the bacterial cells are grown under conditions in which the conditional replication shuttle vector cannot replicate and in which cells that contain the second and third marker genes are selected for. Alkaline lysis of these bacterial cells is then performed to isolate the purified BBPAC DNA.

In addition the present invention also provides an embodiment that further includes a method of transcribing one or more exons of the trappable eukaryotic gene contained in a BBPAC in a eukaryotic cell which comprises transfecting the purified BBPAC into a eukaryotic cell and then culturing the eukaryotic cell. When the BBPAC contains a PEU operatively upstream to one or more exons of the trappable eukaryotic gene, the eukaryotic promoter facilitates the transcription of the trappable eukaryotic gene into an mRNA.

A particular embodiment further includes a method of determining the nucleotide sequence of one or more exons of the trappable eukaryotic gene contained in the BBPAC which comprises preparing a cognate cDNA by using the mRNA as a template, and then determining the nucleotide sequence of the cognate cDNA. The nucleotide sequence of one or more exons of the trappable eukaryotic gene contained in the BBPAC is thus determined. In a preferred embodiment of this type, preparing the cognate cDNA is performed by PCR.

The present invention further provides a method of mapping the insertion site of the PEU. In a preferred embodiment of this type, the mapping is performed by pulse field gel electrophoresis. In a related embodiment the mapping is performed by Southern blot.

Still another aspect of the present invention includes methods of preparing a gene map for a BBPAC contig that contains trappable eukaryotic genes. This aspect of the invention comprises introducing a eukaryotic promoter exon/intron units (PEU) in each BBPAC of a BBPAC contig. In one embodiment of this aspect of the invention, the PEU is placed into an existing BBPAC contig. Preferably the PEU is inserted operatively upstream to one or more exons of the trappable eukaryotic gene. More preferably, the PEU is inserted operatively upstream to either all, or all but the first exon of the trappable eukaryotic gene.

In an alternative aspect of the present invention, a BBPAC contig is constructed using vectors containing one or more PEUs, and genomic DNA containing trappable eukaryotic genes is inserted into the vectors to form a BBPAC contig with BBPACs having one or more PEUs and trappable eukaryotic genes. Preferably a PEU is operatively upstream to one or more exons of the inserted trappable eukaryotic gene. More preferably, the PEU is operatively upstream to all, or all but the first exon of the inserted trappable eukaryotic gene.

The trappable eukaryotic gene(s) for this aspect of the invention can be any eukaryotic gene including vertebrate genes, preferably mammalian genes, and more preferably human genes; invertebrate genes, preferably insect genes; or plant genes.

The insertion of the PEU into the BBPAC is preferably performed by one of the methods of placing a PEU operatively upstream to a trappable eukaryotic gene contained in a BBPAC described herein. The BBPACs are then isolated and transfected into eukaryotic cells, which are cultured. When the BBPAC contains a PEU operatively upstream to a trappable eukaryotic gene, the eukaryotic promoter facilitates the transcription of the trappable eukaryotic gene into an MRNA. Preferably, cognate cDNAs are prepared using the mRNAs as a template and the physical location of each gene is assigned within the BBPAC by hybridization of the cognate cDNAs to the BBPACs of the BBPAC contig. Alternatively the mRNAs can be used in the hybridization. In one such embodiment, RNA probes are generated e.g., from the cDNA, and are used in in situ hybridization determinations. In any case, preferably the BBPAC contig is a BAC contig.

Still another aspect of the present invention provides methods of constructing a cDNA library from genomic DNA, comprising trappable eukaryotic genes, contained in a BBPAC genomic library. Prior to, or alternatively as part of one such embodiment, a BBPAC genomic DNA library is subdivided into individual BBPAC genomic sub-libraries, wherein the BBPACs of the BBPAC sub-library contain trappable eukaryotic genes. Thus in one embodiment the BBPAC genomic library is subdivided into a sub-library that comprises 20 to 1000 BBPACs. In an alternative embodiment the BBPAC genomic library is subdivided into a sub-library comprising 40 to 500 BBPACs. In still another embodiment the BBPAC genomic library is subdivided into a sub-library comprising 80 to 250 BBPACs. In a preferred embodiment the BBPAC genomic library is subdivided into a sub-library comprising 100 to 200 BBPACs. In another preferred embodiment the BBPAC genomic library is subdivided into a sub-library comprising 20 to 80 BBPACs. In preferred embodiments the BBPAC genomic library is a BAC library.

The genomic libraries for this aspect of this aspect of the invention can derived from any eukaryotic genome including a vertebrate genome, preferably a mammalian genome, and more preferably the human genome; an invertebrate genome, preferably an insect genome; or a plant genome.

PEUs are placed into the BBPACs of a BBPAC sub-library. The insertion of the PEU into the BBPAC is preferably performed by one of the methods of placing a PEU in a BBPAC described herein. The BBPACs are then isolated, transfected into eukaryotic cells, and the eukaryotic cells are cultured. When the BBPAC contains a PEU operatively upstream to one or more exons of a trappable eukaryotic gene, the eukaryotic promoter facilitates the transcription of the exon(s) of the trappable eukaryotic gene into an mRNA. Cognate cDNAs are prepared using the mRNAs as a template. A related embodiment further comprises determining the nucleotide sequence of the cognate cDNA. The nucleotide sequences of the exons of the trappable eukaryotic genes contained in the BBPAC genomic library are thus determined.

Accordingly, it is a principal object of the present invention to provide a method for sequencing trappable eukaryotic genes contained in BBPAC genomic libraries.

It is a further object of the present invention to provide a method of introducing a PEU (preferably a BPEU) operatively upstream to a trappable eukaryotic gene contained in a BBPAC.

It is a further object of the present invention to provide a method of obtaining bacterial cells that contain a BBPAC comprising a PEU operatively upstream to a trappable eukaryotic gene.

It is a further object of the present invention to provide a method of procuring isolated BBPACs containing a PEU and a trappable eukaryotic gene.

It is a further object of the present invention to provide a method of transcribing a trappable eukaryotic gene.

It is a further object of the present invention to provide a method of determining the sequence of the transcribed trappable eukaryotic gene.

It is a further object of the present invention to provide a method of providing a gene map for a BBPAC contig.

It is a further object of the present invention to provide a map of the insertion sites of a PEU placed into a BBPAC.

It is a further object of the present invention to provide a cDNA library from a BBPAC eukaryotic genomic library.

It is a further object of the present invention to provide a method of sequencing a cDNA library prepared from a BBPAC eukaryotic genomic library.

These and other aspects of the present invention will be better appreciated by reference to the following drawings and Detailed Description.

BRIEF DESCRIPTION OF THE DRAWINGS

FIG. 2A shows a schematic representation of targeting the BPEU to a BAC/PAC (BBPAC) vector backbone. The eukaryotic genomic genes (depicted as Genes 1, 2, and 3) are placed in between two NotI sites. Most genes contain a poly-adenylation (PolyA) signal sequence. The BPEU is inserted outside of the region included in between the two NotI sites.

FIG. 2B shows a schematic representation of the targeted gene trap. In the schematic two BPEUs are inserted into the BBPAC backbone, outside of the region included in between the two NotI site. The BPEU on the left has trapped Gene 1 (i.e., Gene 1 is under the control the bi-directional promoter of the BPEU) whereas the BPEU on the right has trapped Gene 1. The bi-directionality of the promoters is demonstrated in the schematic. Note, the first exon of the Genes is not trapped, because the first exon of a gene does not contain a 3' splice acceptor.

DETAILED DESCRIPTION OF THE INVENTION

Figure 1A:
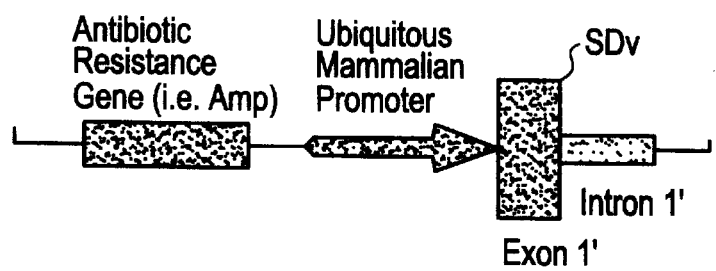
FIG. 1A shows a schematic representation of a Promoter Exon/Intron Unit (PEU) with an antibiotic resistance gene. The PEU comprises a ubiquitous mammalian promoter as a driving promoter, a 5' vector-derived exon, and an intron, wherein the 5' vector-derived exon is adjacent to the intron and under the control of the driving promoter. $SD_v$ stands for the vector derived splice donor.

The present invention provides a novel procedure for determining the nucleotide sequence of all but the first exon of a eukaryotic gene. Furthermore, the methodology allows the determination of essentially all of the exons of any selected eukaryotic genome. The present invention thus provides a facile method for identifying genes in a eukaryotic genome, including the human genome.

Heretofore, sequencing the exons in a particular genome relied on procuring the mRNAs that had been transcribed, or alternatively required the sequencing of genomic DNA. In the former case, genes that are solely transcribed in obscure tissues and/or are rarely transcribed, are likely to be missed. In the latter case, exon-trapping represents the most unbiased methodology to date. However even this technique is limited due to its lack of ability to process more than about a single exon of a gene at one time. The present invention therefore provides an alternative genomic sequencing methodology which instead of being limited to lone exon trapping, essentially allows full gene trapping.

The present invention further exploits the stability of BBPACs to ensure that the trapped eukaryotic gene is an endogenous gene, not an artifactural chimeric gene. In addition, unlike the smaller plasmids used heretofore, recent evidence indicates that BBPACs are large enough to contain the necessary elements for DNA replication and nuclear retention in eukaryotic cells. Thus BBPACs are maintained as stable episomal plasmids when introduced into eukaryotic cells, allowing gene trapping to be performed in a variety of cell lines.

The new methodology of the present invention can also be directly applied to BBPAC contigs. The use of BBPAC contigs can increase the efficiency of gene trapping, since many BBPACs contain multiple genes and the insertion of a single PEU into a BBPAC can maximally trap only one gene, and even the use of a BPEU can only allow the trapping of two genes (assuming the genes are in the proper orientation). Thus any additional genes contained by the BBPAC will be missed. Therefore, the present invention further provides a method of targeted gene trapping employing BBPAC contigs, which contain sets of BBPACs having multiple overlapping genomic DNAs. Performing targeted gene trapping on such a set of BBPACs can result in obtaining essentially all of the genes in the region.

In addition a mini-gene trap cDNA library can be generated through the gene trapping methodology of the present invention. Each gene then can be readily assigned to a physical location within a BBPAC contig by hybridization to the BBPAC library. In this manner essentially all of the genes of a given genomic DNA can be mapped. In addition the resulting cDNAs can be directly used for further biological experimentation. Furthermore, multiple BBPACs in the contig can be pooled to perform the gene trap technology of the present invention at once. Thus the gene trap methodology of the present invention is not only useful for making transcriptional maps for positional cloning projects, but is also valuable for building gene maps from a BBPAC physical map. Such a gene map can be used in genome projects, including the human genome project.

Furthermore, the gene trap methodology of the present invention can also be used to generate a cDNA library from genomic DNA. The present invention provides a method of constructing a cDNA library from the genomic DNA from any eukaryotic source, irrespective of the in vivo gene expression patterns and levels. Therefore, a gene trap cDNA library can be constructed to contain an essentially complete set of exons from any selected genome.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual,* Second Edition (1989) Cold Spring Harbor Laboratory Press, Cold Spring Harbor, New York (herein "Sambrook et al., 1989"); *DNA Cloning: A Practical Approach,* Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology,* John Wiley & Sons, Inc. (1994).

As used herein an "IOBCV" is an independent origin based cloning vector. One example of such a cloning vector is a BBPAC defined below. An IOBCV generally comprises a nucleic acid insert which either is or contains one or more eukaryotic genes. The present invention includes methodology for inserting a eukaryotic promoter exon/intron unit (PEU) operatively upstream of the eukaryotic gene. This facilitates the transcription of all but the first exon of the eukaryotic gene, when the IOBCV is placed into a eukaryotic cell. A "vector" is a replicon, such as a plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

As used herein, a "Bacterial or Bacteriophage-Derived Artificial Chromosome" or "BBPAC" denotes a vector that is derived from a bacterium or bacteriophage such as a Bacterial Artificial Chromosome (BAC) which is an *E. coli* F element based cloning system, a P1-Derived Artificial Chromosome (PAC) or a bacteriophage-based gnomic vector. In one embodiment, the BBPAC encodes up to 700 kilobases of genomic sequences. In a preferred embodiment, the BBPAC encodes between 120 to 180 kilobases of genomic sequences. In one particular embodiment the BBPAC encodes 130 kilobases of genomic sequence.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into MRNA. The MRNA may then be spliced and translated into the protein encoded by the coding sequence.

As used herein a "trappable eukaryotic gene" is a portion of a eukaryotic gene that minimally contains one exon of the gene which has a 3' splice acceptor. Preferably it also contains (or encodes) a 3' polyadenylation sequence. Since neither the first exon of a gene, nor the sole exon of a gene that has only one exon contains a 3' splice acceptor, neither can be included in a trappable eukaryotic gene. A trappable eukaryotic gene can contain all of the exons of the gene that have 3' splice acceptors, i.e., all of the exons other than the first exon. A BBPAC contains a trappable eukaryotic gene when it comprises an entire eukaryotic gene which has at least one exon with a 3' splice acceptor; or a fragment of the gene which minimally contains one exon of the gene that has a 3' splice acceptor, i.e., other than the first exon, and preferably a 3' polyadenylation sequence.

A eukaryotic promoter (or a eukaryotic promoter exon/intron unit (PEU)) is operatively upstream of an exon (and conversely the exon is therefore operatively downstream of the eukaryotic promoter or PEU) if the exon is under the control of the eukaryotic promoter when the promoter and exon are placed into a eukaryotic cell e.g., when the transcription of the exon can be initiated in a eukaryotic (e.g., a mammalian, or a plant) cell by the binding of RNA polymerase to the eukaryotic promoter. The eukaryotic promoter thereby facilitates the transcription of the exon in a eukaryotic cell.

A PEU that is operatively upstream of an exon of the trappable eukaryotic gene (and the exon of the trappable eukaryotic gene is therefore operatively downstream of the PEU) if the exon of the trappable eukaryotic gene is under the control of the PEU when the trappable eukaryotic gene and the PEU are placed into a eukaryotic cell e.g., when the transcription of the trappable eukaryotic gene can be initiated in a eukaryotic cell by the binding of RNA polymerase to the eukaryotic promoter. The eukaryotic promoter thereby facilitates the transcription of the trappable eukaryotic gene in a eukaryotic cell. Depending on the position of the PEU relative to the exons of the trappable eukaryotic gene, the transcription of more than one exon of the trappable eukaryotic gene can be facilitated. In a preferred embodiment, the PEU is operatively upstream from all, or all but the first exon of the trappable eukaryotic gene, thereby facilitating the transcription of all but the first exon.

A "PEU" is a eukaryotic promoter-5' Exon/Intron Unit comprising a eukaryotic promoter, one or more 5' exons (also termed herein a "vector-derived exon"), and an intron. A 5' vector-derived exon is adjacent to an intron and downstream to the eukaryotic promoter. In addition, a PEU can further contain a marker gene. In a preferred embodiment the eukaryotic promoter of the PEU is a bi-directional eukaryotic promoter and the PEU is termed a "BPEU". The bi-directional eukaryotic promoter can be either a single promoter which functions bidirectionally, or preferably one constructed by placing two unidirectional promoters in the BPEU in opposite orientations. Generally these two promoters are identical, except for their orientation. In any case, the BPEU is constructed to contain two sets of vector-derived exons with their corresponding introns, as described above, with each set being downstream and in the operable orientation relative to their corresponding eukaryotic promoter. The term PEU is meant to include both single-directional, and bi-directional eukaryotic promoter-5' Exon/Intron Units. Therefore as used herein, a BPEU is one type of PEU.

A "BBPAC contig" contains BBPACs comprising overlapping genomic fragments, e.g., a "BAC contig" contains BACs comprising overlapping genomic fragments.

As used herein a "gene of interest" is a gene contained by a host cell genome or more preferably an independent origin based cloning vector that has been selected to undergo homologous recombination with a specific nucleic acid contained in a recombination cassette. A gene of interest can be either specifically placed into the host cell or independent origin based cloning vector for this purpose, or can already contained by the host cell or independent origin based cloning vector.

As used herein a "marker" is an indicator, whose presence or absence can be used to distinguish the presence or absence of a particular nucleic acid and preferably the corresponding presence or absence of a larger DNA which contains and/or is linked to the specific nucleic acid. In a preferred embodiment the marker is a protein or a gene encoding the protein, and thus can be more specifically termed a "marker protein" or a "marker gene". The term "marker" (and thus marker protein or marker gene) is meant to be used extremely broadly and includes fluorescent proteins such as green fluorescent protein, enzymes such as luciferase, and further includes drug resistant proteins, whose presence or absence may not solely be regarded as a means to detect cells that contain the drug resistance protein; and/or the genes that encode such proteins. However, drug resistance proteins and/or their corresponding genes can allow the preferential growth of cells that contain the drug resistant gene (or alternatively allow the counter-selection of cells that do not contain the drug resistant gene) and therefore bestow a type of selectable distinction which is meant to fall within the present definition of a marker.

The term "a gene which encodes a marker protein" is used herein interchangeably with the term "marker protein gene" and denotes a nucleic acid which encodes a marker protein.

A "cassette" refers to a segment of DNA that can be inserted into a vector at specific restriction sites. The segment of DNA can encode a particular polypeptide and/or contain a PEU. The cassette and restriction sites are designed to ensure insertion of the cassette in the proper reading frame for transcription and translation, when required. The present invention provides a "recombination cassette" that includes two homology fragments interrupted by a PEU and/or a PEU with a nucleic acid which encodes one or more marker proteins.

As used herein a recombinant deficient host cell is "RecA−" when the host cell is unable to express a RecA-like protein, including recA itself, which can support homologous recombination. In the simplest case, the gene encoding the RecA-like protein has been deleted in a RecA host cell. Alternatively the RecA-host cell contains a mutation in the recA gene that impairs its function.

A "RecA-like protein" is defined herein to have the meaning generally accepted in the art except as used herein the recA protein itself is included as being a specific RecA-like protein. RecA-like proteins are proteins involved in homologous recombination and are homologs to recA [Clark et al., *Critical Reviews in Microbiology* 20:125–142 (1994)].

The recA protein is the central enzyme in prokaryotic homologous recombination. It catalyzes pairing and strand exchange between homologous DNA molecules, and functions in both DNA repair and genetic recombination [McKee et al., *Chromosoma* 7:479–488 (1996)]. A number of RecA-like proteins have been found in eukaryotic organisms and yeast [Reiss et al.,*Proc.Natl.Acad.Sci.* 93:3094–3098 (1996)]. Two RecA-like proteins in yeast are Rad51 and Dmc1 [McKee et al. (1996) *supra*]. Rad51 is a highly conserved RecA-like protein in eukaryotes [Peakman et al., *Proc.Natl.Acad.Sci.* 93:10222–10227 (1996)].

"Heterologous" DNA refers to DNA not naturally located in the cell, or in a chromosomal site of the cell. Preferably, the heterologous DNA includes a gene foreign to the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogues thereof, such as phosphorothioates and thioesters, in either single stranded form, or a double-stranded helix. Double stranded DNA—DNA, DNA—RNA and RNA—RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

"Homologous recombination" refers to the insertion of a modified or foreign DNA sequence contained by a first vector into another DNA sequence contained in second vector, or a chromosome of a cell. The first vector targets a specific chromosomal site for homologous recombination. For specific homologous recombination, the first vector will contain sufficiently long regions of homology to sequences of the second vector or chromosome to allow complementary binding and incorporation of DNA from the first vector into the DNA of the second vector, or the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal sequence is usually required.

Transcriptional and translational control sequences are DNA regulatory sequences, such as promoters, enhancers, terminators, and the like, that provide for the expression of a coding sequence in a host cell. In eukaryotic cells, polyadenylation signal sequences are control sequences.

A "translocation signal sequence" as used herein refers to a signal sequence that is included at the beginning of the coding sequence for a protein to be expressed on the surface of a cell. This sequence encodes a signal peptide, N-terminal to the mature polypeptide, that directs the host cell to translocate the polypeptide. Translocation signal sequences can be found associated with a variety of proteins native to eukaryotes and prokaryotes, and are often functional in both types of organisms.

Any eukaryotic cell potentially can serve as the source for the genomic DNA to be used in the present invention. The genomic DNA can contain regulatory and intron DNA regions in addition to coding regions; clones derived from cDNA will not contain intron sequences. Sources envisioned by the present invention include all types of eukaryotic cells in the animal and plant kingdom. Particular sources include but are not limited to mammals including humans, chimpanzees, gorillas, orangutans, whales, porpoises, cattle, horses, goats, sheep, dogs, cats, mice, rats, and rabbit; avians including chickens, pigeons, turkeys, parrots, parakeets, and canaries; amphibians such as frogs; fish such as salmon and zebrafish; invertebrates such as insects including bees, beetles, ants, and flies; and plants including trees, grasses, and agricultural crops including corn, wheat, soybeans, peas, carrots, potatoes, and rice.

The present invention provides methods for determining the nucleotide sequence of one or more exons, and preferably all but the first exon, of a eukaryotic gene contained in a BBPAC genomic library. A key aspect of the present invention provides a method of including a promoter-5' Exon/Intron Unit (PEU) (preferably a BPEU) and eukaryotic genomic DNA in a BBPAC. In one aspect of the invention the BBPAC is constructed with a vector that contains a PEU. In another aspect of the invention the PEU is places into a BBPAC that contains eukaryotic genomic DNA. In one embodiment of this aspect of the present invention, the insertion of the PEU into the BBPAC is performed by homologous recombination. In a preferred embodiment of this type is performed as described in U.S. patent application Ser. No. 08/880,966, filed Jun. 23, 1997, which is specifically incorporated herein by reference in its entirety. In another embodiment of the present invention the insertion of the PEU into the BBPAC is performed using a transposon system.

The gene trapping system of the present invention relies on the insertion of an exon/intron unit that comprises a strong promoter, a 5' exon that is adjacent to an intron element, and in preferred embodiments a marker such as a bacterial antibiotic resistance gene. The 5' vector-derived exon can be any initial exon of any eukaryotic gene. Preferably the eukaryotic gene is a mammalian gene. For example, the conventional 5' exon/intron region used in the pSPL3 vector [Buckler et al., *PNAS* 88:4005–4009 (1991)] can be used.

In a preferred embodiment the first exon is the beta-globin first exon, the second exon is a fusion of the second beta-globin exon and the HIV tat exon. These exons are then followed by HIV-tat intron or a fragment thereof. The gene trap system is designed to also trap the polyA signal sequence and therefore a 3' polyA containing exon is specifically not included in the gene trapping system.

The promoter should stimulate strong and ubiquitous expression in most eukaryotic cell types. Preferably the eukaryotic promoter of the PEU will be a strong promoter such as the SV40 promoter, metallothionein-1 promoter, the cytomegalovirus (CMV) promoter, the actin promoter, the cauliflower mosaic virus promoter, and the nopaline synthase promoter. [Broido et al., *Nucl. Acids Res.* 17:7891–7903 (1989)]

More preferably the PEU contains a bi-directional promoter (i.e., the PEU is a BPEU). In this case a single insertion enables trapping of genes that lie in opposite orientations on both sides of the BPEU elements. In addition, a marker such as an antibiotic resistance gene, or a gene encoding green fluorescent protein can also be included in the PEU.

In the case when the insertion of the PEU into the BBPAC is performed by homologous recombination, a particular nucleotide sequence in the BBPAC is selected for PEU insertion. Preferably, the particular nucleotide sequence is in the BBPAC vector backbone, i. e., it is not part of the eukaryotic genomic fragment contained by the BBPAC.

The BBPACs that can be employed in the methods of the present invention are obtainable from a number of sources. For example, *E.coli*-based artificial chromosomes for human libraries have been described [Shizuya et al., Proc. Natl. Acad. Sci. 89:8794–8797 (1992); Ioannou et al., In *Current Protocols in Human Genetics* (ed. Dracopoli et al.) 5.15.1–5.15.24 John Wiley & Sons, New York (1996); Kim et al., Genomics 34:213–218 (1996)]. Libraries of PACs and BACs have been constructed [reviewed in Monaco et al., *Trends Biotechol.*, 12:280–286 (1994)], that are readily isolated from the host genomic background for example by classical alkaline lysis plasmid preparation protocols [Birnboim et al., *Nucleic Acids Res.* 7:1513–1523 (1979)], or alternatively, with the use of a nucleobond kit, a boiling Prep, or by cesium gradient (Maniatis, supra). BAC, PAC, and P1 libraries are also available for a variety of species (e.g. Research Genetics, Inc., Genome Research, Inc., Texas A&M has a BAC center to make a BAC library for livestock and important crops). BACs also can be used as a component of mammalian artificial chromosomes.

In addition, the BBPACs can be constructed from vectors containing PEUs. [See Shizuya et al., *Proc. Natl. Acad. Sci.* 18:8794–8797 (1992); and Kim et al., Genomics 34:213–218 (1996), the contents of which are hereby incorporated by reference in their entireties]. The PEUs can be inserted into the vectors by known methodology including homologous recombination e.g., by means described in U.S. Ser. No. 08/880,966, filed Jun. 23, 1997.

BBPAC contigs are available from various Genome projects, including the Human Genome Project.

Bacterial cells that can be used to manipulate the BBPACs include any bacterial cell that can support the BBPAC and the shuttle vector, preferably the original BBPAC host cell.

Most mammalian cells can be used to transcribe trappable eukaryotic genes contained in the BBPACs including COS cells and 3TC cells. Plant cells include tobacco plant cells such as *Nicotiana plumbaginifolia,* and *Nicotiana benthamiana.*

In particular instances, when a PEU is inserted into a selected locus of the BBPAC, the region of insertion can be mapped for restriction enzyme sites. Whereas subcloning is necessary for detailed mapping, it is generally unnecessary since rough mapping is usually sufficient.

Maxiprep DNA from BBPACs with PEU insertions can be prepared by a number of methods including by cesium gradient, or with commercially available columns (e.g., Nucleobond, etc.) as described in U.S. patent application Ser. No. 08/880,966, filed Jun. 23, 1997 hereby incorporated by reference in its entirety. If a pool of modified BBPACs are to be used for gene trapping, the maxiprep DNA can be prepared from the culture containing the pool of bacteria.

The conditional replication shuttle vectors of the present invention are constructed so as to contain a recombination cassette that can selectively integrate into the nucleotide sequence of the particular nucleotide sequence contained by the BBPAC. Such conditional replication shuttle vectors can be constructed which either contain a marker e.g.,a specific drug resistant gene, or can be subsequently modified to contain one. In a preferred embodiment the drug resistant gene can also be counter-selected against, such as the combination of a tetracycline resistant gene which can be counter-selected with fusaric acid. Alternatively, in addition to the drug resistant gene the conditional replication shuttle vector can also contain a counter-selection gene such as a gene that confers sensitivity to galactose, for example. More preferably the conditional replication shuttle vector is a temperature sensitive shuttle vector (TSSV) that replicates at a permissive temperature, but does not replicate at a non-permissive temperature. In a particular embodiment, the permissive temperature is 30° C., and the non-permissive temperature is 43° C. The TSSV is diluted out when the host cell is grown at the non-permissive temperature.

The conditional replication shuttle vectors of this aspect of the present invention should also contain at least one unique cloning site. When a building vector is used for the construction of the recombination cassette as described below, one unique site is reserved for transferring the recombination cassette containing the specific nucleic acid from the building vector to the conditional replication shuttle vector. For example a polylinker can be inserted between two specific restriction sites to create additional restriction sites that allow cloning of the recombination cassette into the conditional replication shuttle vector. In any case the conditional replication shuttle vector created should minimally contain a recombination cassette comprising the PEU flanked at both the 5' and 3' ends by genomic fragments, preferably containing 250 basepairs or more of the particular nucleotide sequence of the BBPAC.

In certain cases a building vector is used to construct the recombination cassette. Two small genomic fragments, each containing about 350 basepairs (250 basepairs to 600 basepairs is sufficient) of the particular nucleotide sequence are cloned into the building vector (e.g., pBV1) in appropriate order and orientation to generate the flanking regions of the recombination cassette. The PEU (and if desired, DNA containing a promoter sequence 5' to a particular nucleotide sequence encoding a marker protein, and/or recA etc.), is inserted between the two genomic fragments in the proper orientation. The recombination cassette is then transferred into the conditional replication shuttle vector (e.g., pSV1.RecA). The recombination cassette, the RecA-like protein gene if present, and the gene for the marker protein, are linked together on the conditional replication shuttle vector such that when the PEU integrates into the particular nucleotide sequence, the RecA-like protein gene and the gene encoding the marker protein remain linked together, and neither the RecA-like protein gene nor the gene encoding the marker protein remain linked to the integrated PEU. The PEU itself preferably includes a gene encoding a marker protein which is constructed to remain linked to the integrated PEU.

In a preferred embodiment the conditional replication shuttle vector is a TSSV. In a one such embodiment the TSSV is pSV1.RecA having the ATCC no. 97968, which is modified to contain a PEU as described above.

The BBPAC is preferably contained in a recombination deficient host cell. In such embodiments neither the BBPAC alone, nor the BBPAC in combination with the host cell, can independently support homologous recombination. In a particular embodiment of this type both the BBPAC and the host cell are RecA⁻, and inducing the host cell to transiently support homologous recombination comprises inducing the transient expression of the RecA-like protein to support homologous recombination in the host cell. However, as any person skilled in the art would readily understand, alternative causes for recombination deficiency may be rectified by methods that are analogous to those taught by the present invention and/or readily apparent in view of such teachings. For example recombination deficiency may be due to a deficiency of an alternative recombination protein such as another Rec protein including recB, recC, recD, and recE [Clark et al., *Critical Reviews in Microbiol.* 20:125–142 (1994)] which may be manipulated in a manner that is analogous to that taught herein for RecA-like proteins.

In the case of a RecA⁻ host cell, inducing the host cell to transiently support homologous recombination comprises inducing the transient expression of a RecA-like protein in the host cell. Such induction may be performed by expressing a RecA-like protein contained by the recombination deficient host that is under the control of an inducible promoter.

Preferably inducing the transient expression of the RecA-like protein is performed with a conditional replication shuttle vector that encodes the RecA-like protein. Such conditional replication shuttle vectors can be constructed by inserting a PCR amplified RecA-like gene, when desired, into an appropriate conditional replication shuttle vector which either contains a specific marker protein gene e.g., a drug resistant gene, or can be subsequently modified to contain one. Conditional replication shuttle vectors can also include pBR322 in a polyA temperature-sensitive bacterial strain.

Inducing the transient expression of the RecA-like protein consists of transforming the host cell with the TSSV at a permissive temperature, and growing the host cell at a non-permissive temperature. The TSSV encodes a RecA-like protein that is expressed in the host cell and supports the homologous recombination between the recombination cassette and the particular nucleotide sequence contained in the BBPAC. The TSSV encoding the RecA-like protein is diluted out when the host cell is grown at the non-permissive temperature.

The RecA-like protein of a conditional replication shuttle vector can be controlled by either an inducible promoter or a constitutive promoter. In one particular embodiment the transient expression of the RecA-like protein is achieved by the transient induction of the inducible promoter in a host cell. In another embodiment, the constitutive promoter is the endogenous *E. coli* recA promoter.

According to the methods of the present invention a RecA⁻ host cell containing the BBPAC is transformed with the conditional replication shuttle vector. The BBPAC can also contain a marker gene which bestows resistance to a host cell against a corresponding toxic agent/drug such as an antibiotic or in a specific embodiment, chloramphenicol. The cells are grown under the conditions in which the conditional replication shuttle vector can replicate (e.g., when the conditional replication shuttle vector is a TSSV which replicates at 30° but not at 43°, the host cell is grown at 30° C.) and the transformants can be selected via the specific drug resistant gene (or first marker protein gene) carried by conditional replication shuttle vector, and the marker protein gene carried by the BBPAC. Since the conditional replication shuttle vector also carries the RecA-like protein gene, homologous recombination can occur between the conditional replication shuttle vector and BBPAC to form co-integrates through the sequence homology at either the 5' or the 3' flanking regions of the recombination cassette. The co-integrates then can be selected by growing the cells on plates containing the drugs specific for the first and second drug resistance genes, at non-permissive conditions (e.g. for the TSSV above, at 43° C.) so that the non-integrated, free conditional replication shuttle vectors are lost. This results in the selection for host cells carrying the integrated conditional replication shuttle vectors, (which co-integrate either into the BBPAC or into the host chromosome). Correct BBPAC co-integrates can be identified by PCR or more preferably with Southern blot analyses.

The co-integrates can then be re-streaked onto plates containing the second drug, (i.e., the drug which the gene initially carried by the BBPAC protects against) and grown under non-permissive conditions overnight. A fraction of the co-integrates undergo a second recombination event (defined as resolution), through sequence homology at either the 5' or the 3' flanking regions of the recombination cassette. The resolved independent origin based cloning vector automatically loses both the first drug resistant gene (i.e., the specific drug resistant gene contained by the conditional replication shuttle vector) and the RecA-like protein gene due to the linkage arrangement of the RecA-like protein gene, the drug resistant gene and the PEU on the conditional replication shuttle vector, described above. In addition, the excised conditional replication shuttle vector cannot replicate under the non-permissive conditions and is therefore diluted out.

The resolved BBPAC can be further selected for by growing the host cells (e.g., at 37° C.) on plates containing the second drug and an agent that counterselects against cells containing the gene resistant to the first drug (e.g., a gene conferring tetracycline resistance may be counterselected against with fusaric acid). The resolved BBPAC will be either the original BBPAC or the BBPAC containing the PEU.

One method to identify the correctly resolved BBPAC is to choose 5–10 colonies and prepare a miniprep DNA. The DNA can then be analyzed using Southern blots to detect the correct targeting events.

In a preferred embodiment the BPEU element also contains a marker such as an antibiotic resistance gene (e.g. ampicillin) that remains with the PEU upon integration into the BBPAC. This marker can be used to identify BBPACs that contain the PEU. In this case the co-integration and resolution steps of the targeted BBPAC modification can be simplified by adding a selection requirement for this additional antibiotic resistance. Such methodology can obviate the need to perform Southern blot analyses. This feature also permits the simultaneous modification of a pool of BBPACs.

The marker can be a marker gene that encodes a marker protein that confers a specific drug resistance to the host cell, as exemplified above, against drugs such as antibiotics, e.g., ampicillin, chloramphenicol, and tetracycline, a protein that confers a particular physical characteristic to the cells, such as a green fluorescent protein or a modified green fluorescent protein as described in U.S. Pat. No. 5,625,048, Issued Apr. 29, 1997 and WO 97/26333 Published Jul. 24, 1997 hereby incorporated by reference in their entireties, or an enzyme such as luciferase. Alternatively, it can be another marker protein including e.g., B-galactosidase.

In preferred embodiments the methods of homologous recombination are selective, and nonspecific nucleotide sequence rearrangements either do not occur, or are essentially undetectable by one or more conventional methods of analysis. One such method includes pulsed field gel mapping of the BBPAC containing a PEU and the unmodified BBPAC to determine whether any unexpected deletions, or insertions or rearrangement were generated during the modification procedure. In one particular embodiment, the same filter can be probed separately with a probe for the whole independent BBPAC, with a probe for the particular nucleotide sequence, or a probe for the PEU. A restriction enzyme digestion can reveal a finger print of the modified BBPAC indicating whether the fragments are preserved. Restriction enzyme digestions can be repeated with one or more additional restriction enzymes selected with respect to the restriction site map of the BBPAC In an alternative method, the BBPAC can be assayed with both a probe specific for any region of the DNA contained by the recombination cassette predicted to be inserted into the independent origin based cloning vector (e.g., the PEU) and a probe specific for a region outside of the modification region (e.g., outside of the PEU).

A BBPAC of the present invention can be purified by gel filtration, e.g. a column filled with SEPHAROSE CL-4B yielded intact linear BAC DNA. The column can be pre-equilibrated in an appropriate buffer as described in U.S. patent application Ser. No. 08/880,966, filed Jun. 23, 1997 and hereby incorporated by reference in its entirety. The purified DNA can be directly visualized with ultraviolet light after ethidium bromide staining, for example. Columns such as the SEPHAROSE CL-4B column also can efficiently separate degraded DNA from the pure linear DNA.

The BBPAC of the present invention can be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, *J. Biol. Chem.* 267:963–967; Wu and Wu, 1988, *J. Biol. Chem.* 263:14621–14624; Hartmut et al., Canadian Patent Application No. 2,012,311, filed Mar. 15, 1990). Preferably the modified BBPACs are introduced by a psoralen-inactivated adenovirus as carrier as described by [Baker et al., *NAR* 25:1950–1956 (1997)]. Essentially any cell line can be used since BBPACs replicate in mammalian cells and the SV40 promoter is active in the majority of mammalian cells.

The present invention also provides methods of performing randomized gene trapping. One such embodiment is based on the insertion a PEU (preferably a BPEU) into a BBPAC through the use of a transposon system. The PEU element is initially placed into a plasmid, preferably a conditional replication shuttle vector, that contains a mini-transposon. The BPEU is specifically located between the inverted repeat ends of the transposon. When a marker is included in the BPEU, the marker is also located in between the transposon ends.

A gene encoding transposase is located outside of the inverted repeat ends of the transposon on the shuttle vector. In a preferred embodiment, the gene encoding transposase is under the control of an inducible promoter. In this case, the inducible promoter is also outside of the inverted repeat ends of the transposon on the shuttle vector. In a preferred embodiment of this type the inducible promoter is the P-galactosidase (lac) promoter which can be induced by IPTG (isopropyl-β-D-thiogalactopyranoside) and is kept fully repressed in the absence of the inducer by the constitutive expression of lacI$^q$ by either the host cell (e.g., DH10B, which expresses lacI$^q$ constitutively at high levels) or the conditional replication shuttle vector. Of course other inducible promoters that can be used.

In one embodiment a bacterial host cell containing the BBPAC is transformed by a shuttle vector e.g., a TSSV such as pSV.TN10.RGT exemplified below, containing transposase under the control of an inducible promoter, and a PEU (preferably a BPEU having a marker) which is inserted in the TSSV in between the inverted ends of the transposon. A transformed host cell can be selected for having markers contained on the BBPAC, the shuttle vector and the PEU (contained by the shuttle vector). Treatment of the host cells with an inducer for the inducible promoter transiently induces the expression of the transposase, which in turn, induces the transposition of the PEU into the BBPAC and the bacterial host cell genome. Although the majority of the mini-transposons insert into the bacterial genome, this is unimportant. In one such embodiment the induction is controlled such that each BBPAC receives only a single transposon or no transposon at all.

Following the insertion of the transposon, the shuttle vector is eliminated from the bacterial host. In one embodiment the shuttle vector is a conditional replication shuttle vector and the host cells are grown under conditions in which the shuttle vector cannot grow, e.g., at a non-permissive temperature such as 43° C., when the conditional replication shuttle vector is a TSSV which cannot replicate at 43° C. The TSSV will not replicate and therefore be diluted out and lost. In this case, the markers on the BBPAC and the PEU preferably are also selected for.

In another embodiment, the host cells are grown under conditions in which cells containing the shuttle vector can be selected against (e.g., the shuttle vector can contain a tetracycline resistance gene, and the host cells can be grown in fusaric acid). In this example, the Tet resistance gene is placed on the shuttle vector such that it is physically outside of the transposon inverted repeats of the shuttle vector, and therefore, the Tet resistance gene is not transported by the transposon. Therefore the selection for the loss of tetracycline resistance is equivalent to the selection for loss of the shuttle vector. Again, the markers on the BBPAC and the PEU are preferably selected for during this step of the procedure.

Preferably, the shuttle vector is a conditional replication shuttle vector that contains a marker that can be counter-selected against (e.g., the Tet resistance gene) and the elimination of the shuttle vector includes both growing the host cells under conditions in which the conditional replication shuttle vector cannot replicate, and under conditions in which the host cells containing the shuttle vector can be selected against. In one such embodiment, these two discriminating features are performed in two separate steps, e.g., when the counterselecting agent is used, the host cell is be grown under conditions that allow the shuttle vector to replicate, (in the case of the TSSV exemplified above, at 37° C.).

Once the shuttle vector is removed, all bacteria which contain the markers of the BBPAC and the PEU also must contain a minitransposon insertion, either in the bacterial chromosome or in the BBPAC. The supercoiled BBPAC DNA can be isolated from the host cells by conventional alkaline lysis. Since the BBPAC is the only circular plasmid in the bacteria the DNA prep only contains the circular BBPAC DNA. The circular BAC DNA can be electroporated into competent bacterial cells e.g., according to the protocol described by Sheng et al. [*NAR* 23, 1990–1996 (1995)], and the cells can then be are selected for the markers contained by the PEU and the BBPAC.

The greater the number of cells chosen, the more PEU integration sites within the BBPAC are obtained, and therefore, the more trappable eukaryotic genes obtained. In one embodiment the insertion site of the PEU element can be mapped by pulsed field gel electrophoresis and Southern blots. The BBPACs are then ready for placing into eukaryotic cells as described herein.

Transposon systems appropriate for use in the present invention include Tn3, and Tn10 [Chatterjee et al., *Genet. Anal Biomol. Eng.*, 13:33–42 (1996)] hereby incorporated by reference in its entirety. The mini-Tn10 transposon with an inducible transposase for example, can insert a 10 kb nucleic acid sequence located between the inverted repeats into relatively random locations [Chatterjee et al., *Genet. Anal. Biomol. Eng.*, 13:33–42 (1996); Chatterjee et al., *NAR*, 25:2205–2212 (1997)].

Shuttle vectors that contain a nucleotide sequence that encode transposase under the control of a inducible promoter, a promoter Exon/intron unit (PEU) and a pair of inverted transposon ends are also part of the present invention. The PEU is positioned in between the pair of inverted transposon ends. The shuttle vector is preferably a condition replication shuttle vector and more preferably a temperature sensitive shuttle vector (TSSV). In a preferred embodiment the promoter is a bidirectional promoter making the PEU a BPEU. In another preferred embodiment the TSSV also contains a gene that confers tetracycline resistance and this is positioned outside of the pair of transposons. In a more preferred embodiment, the TSSV is pSV1.Tn10-RGT which can be readily constructed from pSV1.RecA having the ATCC no. 97968.

The present invention may be better understood by reference to the following non-limiting Example, which is provided as being exemplary of the invention. The following example is presented in order to more fully illustrate the preferred embodiments of the invention. It should in no way be construed, however, as limiting the broad scope of the invention.

EXAMPLE

GENE TRAPPING IN BBPACs

Introduction

Bacterial artificial chromosomes (BACs) and P-1 derived artificial chromosomes (PACs) are large genomic clones that propagate in *E. coli* as circular plasmid [Shizya et al., PNAS 89, 8794–8797 (1992); Ioannou et al., *Nature Genetics*, 6:84–89 (1994)]. BACs and PACs are ideal systems for use in exon trapping. First, BACs and PACs have a cloning capacity of 700 kb [Zimmer and Verrinder Gibbins, *Genomics*, 42:217–226 (1997)], with most libraries having an average insert size of 150 kb. This means that a single BAC can hold most mammalian genes. Therefore, exon trapping performed with a BAC can result in the trapping of all of the exons of the gene including the polyA signal sequence. Thus, instead of exon trapping, the present invention allows gene trapping. Second, BACs are extremely stable, and therefore, chimeric genes are generally not formed, and inserts are rarely deleted. Such high stability ensures that the trapped gene is an endogenous gene, not an artifactural chimeric gene. Third, BACs and PACs exist as circular supercoiled bacterial plasmids, and therefore are extremely amenable to further manipulation. In addition, conventional bacterial plasmid DNA preparation and sequencing methods can be applied to BACs and PACs. Therefore, manipulating BACs and PACs is as simple as manipulating smaller plasmids. Fourth, unlike small plasmids, BACs are large enough to contain the necessary elements for DNA replication and nuclear retention in mammalian cells. When introduced into mammalian cells, BACs are maintained as stable episomal plasmids [Baker and Cotten, *NAR* 25, 1950–1956 (1997)]. This property allows exon trapping to be performed in a variety of cell lines, as opposed to being restricted to COS cell lines, as currently required by conventional exon trapping systems.

Two novel gene trapping systems are described below. The first system, termed "targeted gene trapping", targets the promoter-5' exon elements to a designated location in the BAC by homologous recombination. The second system, termed "randomized gene trapping", employs the same promoter-5' exon element, but the promoter-5' exon element is randomly inserted into a BAC via a Tn 10 transposon system. The resulting collection of BACs are then used for gene trapping.

The following steps are involved in a gene trapping system (Table 1). First, a promoter-5' exon/intron unit is inserted into the BAC containing genomic DNA, either by targeted modification or transposon mediated integration. Then DNA is prepared from the modified BAC and transfected into the desired mammalian cell line. After culturing for a few days, RNA is isolated from these cell lines and oligo dT primed cDNAs are prepared. Then PCR amplification is performed with a 5' vector-exon specific oligo and an oligo dT. The resulting cDNA products are subcloned into a suitable cloning vector. The clones are then sequenced to identify the trapped gene. The cDNAs can be hybridized back to the original BACs to confirm their origin.

TABLE 1

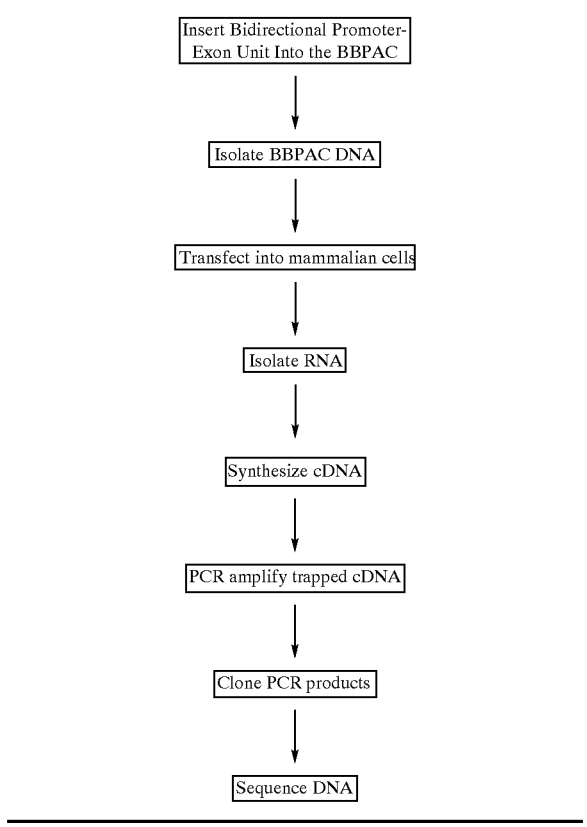

TABLE 2

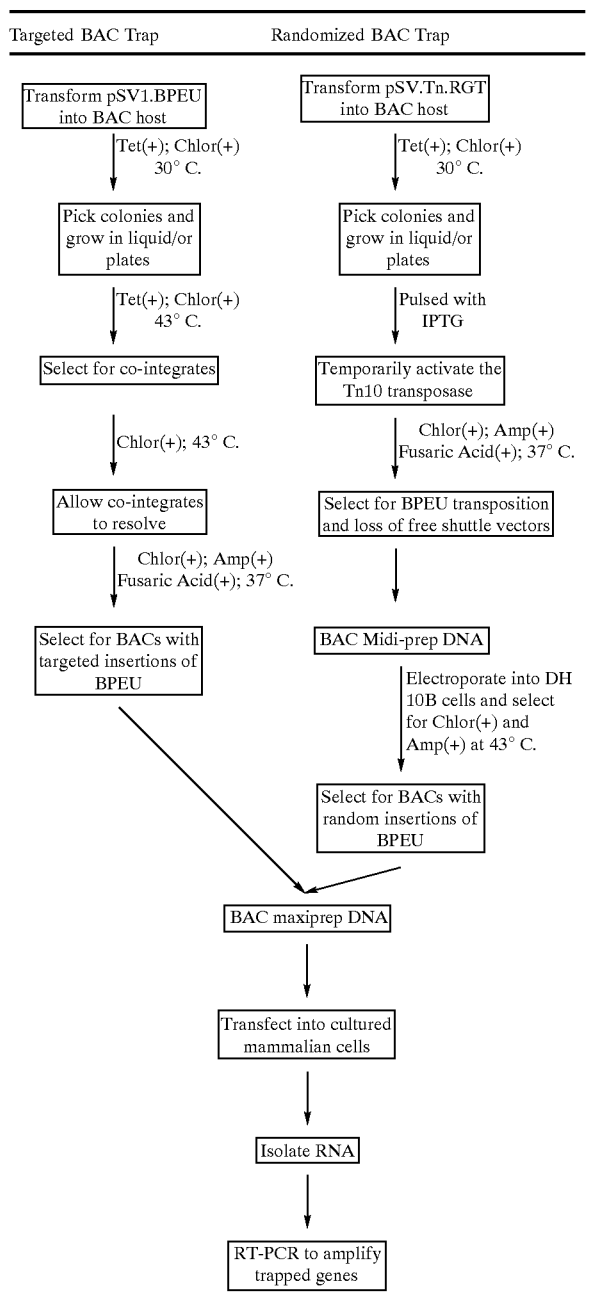

Procedures and Results

I. The promoter-5' Exon/intron Unit (PEU) and the Bidirectional Promoter-5' Exon/intron unit (BPEU): Unlike the conventional gene trapping system, in which small genomic fragments are cloned into multiple cloning sites lying within an intron, the gene trapping system involves insertion of a unit containing a strong promoter such as viral promoters (e.g., CMV) or promoters for housekeeping genes, plus a 5' exon (called a vector-derived exon), adjacent intron elements, and a bacterial antibiotic resistance gene, such as the Amp gene, into the BBPAC (FIG. 1A). The promoter can be any promoter that stimulates strong and ubiquitous expression in most mammalian cell types, including the SV40 promoter, and the metallothionein-1 promoter. The 5' vector-derived exon can be any initial exon of any eukaryotic gene. For example, the conventional 5' exon/intron region used in the pSPL3 vector [Buckler et al., PNAS 88:4005–4009 (1991)] can be used. In this example the first exon is the beta-globin first exon, the second exon is a fusion of the second beta-globin exon and the HIV tat exon. These exons are then followed by HIV-tat intron. A 3'polyA containing exon is specifically not included in the gene trapping system for the following reasons: first, the BBPAC needs to be modified only once to introduce the promoter exon/intron unit (PEU) into the BBPAC; second, this design also allows trapping of the endogenous polyA signal sequence, and therefore all of the exons of the particular gene except the first one; third, since there are no 3' splice acceptor and polyA signal sequences provided (as are provided in the conventional exon trapping system) there is no background due to splicing of the vector exons alone.

The gene trap system is designed to also trap the polyA signal sequence. Therefore, those genes that do not have their polyA signal sequence in a BAC will be missed by the gene trap method. This problem can be solved by using an overlapping set of BACs to do gene trapping. These overlapping sets of BACs essentially guarantee that a BAC exists in the contig that contains the exon with the polyA sequence for any given gene. Therefore, gene trapping using a BAC contig greatly increases the odds that all genes will be identified.

Figure 1B:
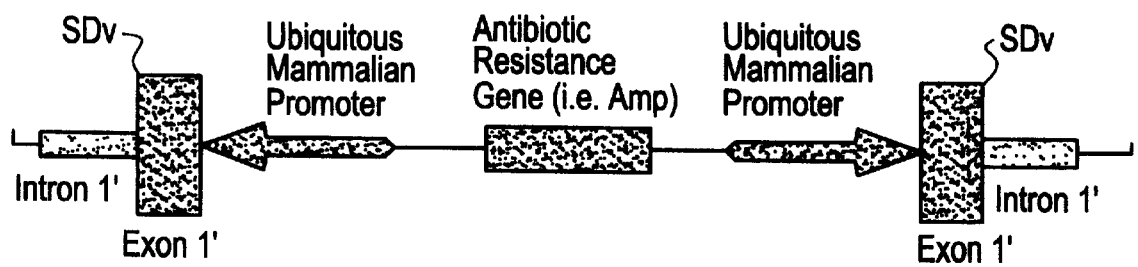
FIG. 1B shows a schematic representation of a Bi-Directional Promoter Exon/Intron Unit (BPEU) with an antibiotic resistance gene.

An improved version of the gene trapping system comprises the insertion of a unit containing a bidirectional promoter-exon/intron (BPEU). In addition, an antibiotic resistance gene can also be included (FIG. 1B). Therefore a single insertion enables trapping of genes that lie in opposite orientations on both sides of the BPEU elements. Due to the higher efficiency of the gene trapping with BPEU, the subsequent steps of gene trapping is further exemplified with insertion of the BPEU elements. However, the same procedures can be followed with a single directional PEU.

II. Targeted gene trapping: Targeted gene trapping refers to the insertion of the BPEU into the designated site within the BBPAC using the targeted BBPAC modification technology disclosed herein, and in U.S. patent application Ser. No. 08/880,966, filed Jun. 23, 1997 incorporated herein in its entirety. The insertion site can be anywhere within the BBPAC, including the genomic insert or the vector sequence, solely depending on the homologous sequence used to target the BPEU element. The total homologous sequence used is optimally about 500 bp or greater. Since for a given BBPAC library, the vector sequence is identical and known, the universal shuttle vector is preferably designed to target the BPEU elements to the vector backbone (see FIG. 2A, the genomic insert of the BBPAC is represented as the sequence between two NotI sites). Since the BPEU element also contains an antibiotic resistance gene (e.g. ampicillin), the co-integration and resolution steps of the targeted BBPAC modification can be simplified by adding a selection requirement for this additional antibiotic resistance. Such methodology can obviate the need to perform Southern blot analyses. This feature permits the simultaneous modification of a pool of BBPACs.

BBPACs containing the BPEUs targeted to the vector backbone can be transfected into eukaryotic cells allowing two genes in opposite transcription orientations to be trapped when the genes are in the proper orientation (see FIG. 2B; the splicing machinery of the cell only traps genes having a 3' splice site acceptor 5' to the Poly A signal sequence). Therefore, when employing a BBPAC containing multiple genes, a single insertion of a BPEU most likely will miss some of the genes (see FIG. 2B, e.g., Gene 2). This problem can be solved using a dense overlapping of set BBPACs (i.e., a BBPAC contig). Performing targeted gene trapping on such a set of BBPACs can result in obtaining essentially all of the genes in the region. Another aspect of this gene trap system is that since it provides the vector-driven first exon and only traps exons with a 3' splice acceptor, it therefore skips the very first exon of a given gene (FIG. 2B). Fortunately, the first exon of a gene seldom contains a coding sequence. This first exon has to be identified by another method, such as by screening cDNA libraries.

Figure 3A:
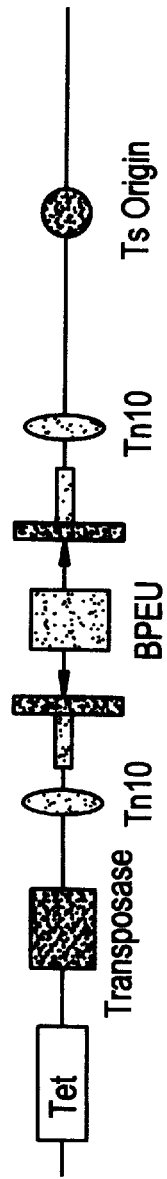
FIG. 3A shows a schematic representation of the structure of the pSV.Tn10-RGT vector. The Randomized Gene Trapping (RGT) shuttle vector contains a tetracycline (Tet) resistance gene, a gene encoding transposase under the control of an inducible promoter (not shown), a temperature sensitive origin of replication, a bi-directional promoter exon/intron unit (BPEU) and a pair of inverted transposon ends. The BPEU is positioned in between the pair of inverted transposon ends.

III. Randomized Gene Trapping: Randomized gene trapping involves the relatively random insertion of a PEU (preferably a BPEU) into a BAC mediated by transposon system (e.g. Tn10 or Tn3). The BPEU element and the bacterial resistant gene, e.g., the Amp gene, is carried by a plasmid that also contains a mini-transposon and a temperature sensitive origin of replication. The use of the Tn-10 system illustrates this mode of randomized gene trapping though there are many other suitable transposon systems. The gene trapping vector using the Tn-10 transposon is further illustrated in FIGS. 3A and 3B using pSV.Tn19-RGT. The BPEU and the Amp gene are located between the inverted 70 bp of the transposon ends. The gene encoding transposase along with its inducible promoter, in this case a lac promoter, is located outside of the inverted repeats. The lac promoter is inducible by IPTG (isopropyl-β-D-thiogalactopyranoside) and therefore, in this system, so the expression of transposase is inducible by IPTG. The rest of the plasmid is composed of a temperature sensitive origin of replication and a tetracycline (Tet) resistance gene, being analogous to the TSSV pSV1.RecA exemplified above, minus the RecA gene. The mini-Tn10 transposon with an inducible transposase previously has been shown to insert a nucleic acid sequence between the inverted repeats (up to 10 kb) into relatively random locations in bacterially propagated large genomic clones [Chatterjee and Sternberg, *Genet. Anal. Biomol. Eng.*, 13:33–42 (1996); Chatterjee and Coren, *NAR* 25, 2205–2212 (1997)].

The following procedure can be used to isolate a nested group of BACs and PACs carrying a single, and relatively randomly inserted BPEU element. In this example, the BBPAC is a BAC containing a fragment of eukaryotic genomic DNA and a chloramphenicol resistance gene. First, a bacterial host cell containing the BAC is transformed by the TSSV, pSV.TN10.RGT. The bacterial host cell is next selected for having resistance to chloramphenicol, and tetracycline. In this example the bacterial host cell is DH10B, which expresses lacI$^q$ constitutively at high levels. Therefore the transposase, which is under the control of the lac promoter, is not expressed. If the bacterial host does not express sufficient level of the lacI$^q$, the lacI$^q$ gene can be cloned into the pSV.Tn10.RGT shuttle vector which then supplies the lacI$^q$ when transformed into bacteria. Treatment of the host cells with IPTG will transiently induce the expression of the transposase, which in turn, induces the transposition of the BPEU element and the Amp resistance gene into the BAC and the bacterial host cell genome. The majority of the mini-transposons insert into the bacterial genome.

The IPTG induction can be carefully controlled such that each BAC will receive only a single transposon or no transposon at all. After the transposon insertion, the pSV.Tn10-RGT plasmid is eliminated from the bacteria. Two methods for eliminating the pSV.Tn10-RGT TSSV which can be used separately, or in tandem are:

(1) the host bacterial cells can be grown at 43° C. in LB with chloramphenicol and ampicillin. The TSSV will not replicate and therefore be diluted out and lost.

(2) the host bacterial cells can be grown at 37° C., and then chloramphenicol, ampicillin and fusaric acid can be added to the media to select for loss of tetracycline resistance. Since the pSV.Tn10.RGT carries the Tet resistance gene and the Tet resistance gene is physically outside of the transposon inverted repeats of the TSSV, the Tet resistance gene is not transported by the transposon. Therefore the selection for the loss of tetracycline resistance is equivalent to the selection for loss of the pSV.Tn10.RGT plasmid.

Figure 3B:
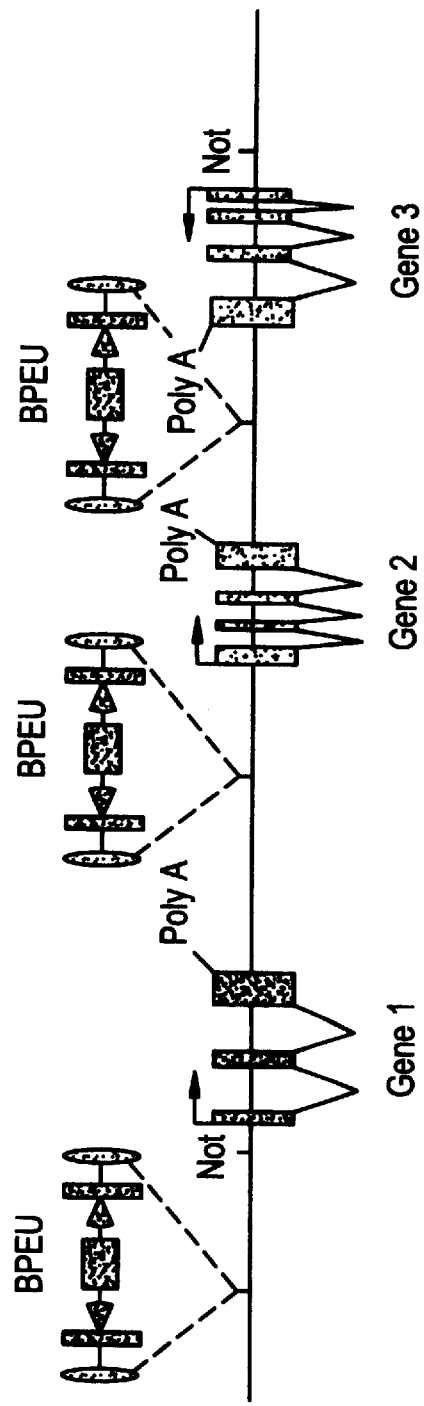
FIG. 3B shows a schematic representation of random integration of multiple BPEUs into a BBPAC.

Once the shuttle plasmid is lost, all bacteria which grow in chloramphenicol and ampicillin have a minitransposon insertion, either in the bacterial chromosome or in the BAC. To isolate those having a transposon insertion in the BAC, the supercoiled BAC DNA can be isolated from the host bacterial cells (and bacterial chromosomes) by conventional alkaline lysis. Since the BAC is the only circular plasmid in the bacteria (the TSSV has been eliminated as described above), the DNA prep only contains the circular BAC DNA (with perhaps a small amount of chromosomal DNA contaminant). The circular BAC DNA is next electroporated into competent DH10B bacterial cells according to the protocol described by Sheng et al. [*NAR* 23, 1990–1996 (1995)], and then DH10B cells are selected for chloramphenicol and ampicillin resistance. Those bacterial that grown on the chloramphenicol and ampicillin plates contain BACs with BPEU elements inserted at relatively random locations within the BAC (FIG. 3B). The more clones picked, the more integration sites within the BAC one obtains, and the more genes one obtains in the subsequent gene trapping. The insertion site of the BPEU element can be optionally mapped by pulsed field gel electrophoresis and Southern blots. The BACs are then ready for gene trapping in eukaryotic cells as described above.

There are several advantages to the randomized gene trap (RGT) system over the target gene trap system. First, one round of modification by RGT of a single BAC can potentially trap all of the genes in the BAC whereas the targeted BAC modification can only trap up to two genes per BAC. Second, the density of BPEU insertion can be easily controlled by the RGT method. Since the transposons insert relatively randomly, by picking increasing number of colonies in the last step, one gets increasing coverage of the BAC with transposon insertions. Such stringency readily can be adjusted for gene rich and gene poor BACs with the RGT method. Third, the pSV1.Tn10 -RGT plasmid can be used for BACs, PACs and P1.

IV. Isolation of maxiprep BBPAC DNA: Maxiprep DNA from BBPACs with BPEU insertions can be prepared by a number of methods including the conventional cesium gradient method, or with commercially available columns (e.g., Nucleobond, etc.) as described in U.S. patent application Ser. No. 08/880,966, filed Jun. 23, 1997. If a pool of modified BBPACs are to be used for gene trapping, the maxiprep DNA can be prepared from the culture containing the pool of bacteria.

V. Transfection of BBPAC DNA into mammalian cells: Maxiprep BBPAC DNA are transfected into appropriate mammalian cell lines using the method described by Baker and Cotten [*NAR* 25, 1950–1956 (1997)], which utilizes the psoralen-inactivated adenovirus as a carrier. This method proved to be more efficient for transfecting BAC DNA into mammalian cells, than conventional electroporation or lipofection, (which are alternative methods). The cell line used can be essentially any cell line, since BACs can replicate on their own in mammalian cells and the SV40 promoter is active in the majority of mammalian cells.

VI. RNA Isolation, cDNA synthesis, PCR amplification, Subcloning of PCR products and sequencing: After the transfection of the mammalian cells with the BACs, the subsequent steps required for completing the gene trapping procedure are similar to those for conventional exon trapping systems [Buckler et al., *PNAS* 88:4005–4009 (1991)]. For example, five to ten days after transfection, RNA can be prepared from the transfected cells using a standard protocol. Then first strand cDNA is synthesized using an oligo dT primer flanked with 10–15 basepairs GC rich sequence, and reverse transcriptase. The first strand cDNA is amplified by PCR using an oligo dA primer and a primer for the HIV-tat exon. The PCR is performed at several conditions to optimize the amplification of the cDNA ranging from 500bp to 3–4 kb. The amplified PCR products are then subcloned into the TA cloning vectors and the trapped gene sequence can be determined by conventional methods.

VII: Conversion of a BBPAC contig into a gene map: Many positional cloning projects and genome projects involve initially making an overlapping set of BBPACs, called a contig, and then identifying genes within the contig. Current methods of identification of genes within the contig include cDNA selection, exon trapping and sequencing. cDNA selection is laborious and dependent on the availability of the RNA source. Exon trapping, is efficient, but often only results in trapping small single exons, and can only work with one BBPAC at a time. Sequencing can potentially identify all of the genes in the BBPAC, but is expensive and relies on the existing cDNA database and search algorithms, which are far from complete. The gene trap strategy of the present invention can be directly applied to BBPAC contigs as a pool. A mini-gene trap cDNA library can be isolated and each gene can be quickly assigned to its physical location within the contig by hybridization to the BBPACs. Advantages of using the gene trap system of the present invention for the generation of a transcript map are: (1) Potentially all of the cDNAs can be isolated, (especially with the randomized gene trapping method). (2) The trapped genes contain multiple exons including the polyA signal sequence, as opposed to the individual exons contained in the vectors of the prior art methods. Thus the cDNAs of the present invention can be directly used for further biological experimentation. (3) Multiple BBPACs in the contig can be pooled to perform the gene trap at once, as opposed to the prior art methods which uses only one BBPAC at a time. (4) The gene trap system of the present invention is simpler and less expensive than direct sequencing. The gene trap system of the present invention not only is useful for making transcript maps in positional cloning projects, but also may be valuable for building gene maps from a BBPAC physical map for use in genome projects, such as the human genome project.

VIII: Gene trap cDNA library (or GT-cDNA library): Construction of a cDNA library frequently depends on the availability of the tissue from which the RNA is isolated. cDNA that are expressed in a tissue which has a limited number of cells (i.e. inner ear or hypothalamus), or expressed at a very specific developmental stage, or expressed at a very low level, could easily be missing in the existing cDNA libraries. Human cDNA libraries for example, are currently available for only a few organs and at only a few different developmental stages. This greatly limits the isolation of the coding sequence of rare human transcripts, which may be particularly important in certain disease states. The present invention overcomes this shortcoming in the prior art by providing a method of constructing a cDNA library from a genomic DNA of any source, irrespective of the expression pattern and level of the genes in vivo. For example, a BAC library, such as the human BAC library, can be divided into pools of 100–200 BACs per pool. Each pool can undergo gene trapping to produce a pool-specific cDNA library. The procedure is repeated until the entire BAC library is converted into a gene-trapped cDNA library. If the stringency of gene trapping is relatively high, the gene trap cDNA library will represent an essentially complete set of genes from any genome.

IX: Constructing BBPACs from vectors containing PEUs.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes, and all molecular weight or molecular mass values, given for nucleic acids are approximate, and are provided for description.

Various publications are cited herein, the disclosures of which are incorporated by reference in their entireties.

What is claimed is:

1. A method of placing a eukaryotic promoter exon/intron unit (PEU) into a Bacterial or Bacteriophaze-Derived Artificial Chromosome (BBPAC) that contains a trappable eukaryotic gene comprising:
   (a) introducing a conditional replication shuttle vector into a host cell containing the BBPAC under conditions in which the conditional replication shuttle vector can replicate and transform the host cell, wherein:
      (i) the BBPAC contains a trappable eukaryotic gene, BBPAC vector DNA, and a second marker gene;
      (ii) the conditional replication shuttle vector contains a RecA-like protein gene, a first marker gene which can be counter-selected against, and a recombination cassette, wherein the recombination cassette comprises a PEU flanked on both its 5' and 3' ends by nucleotide sequences that are homologous to BBPAC vector DNA; wherein the recombination cassette, the RecA-like protein gene, and the first marker gene are linked together on the conditional replication shuttle vector such that when the PEU integrates into the BBPAC, the RecA-like protein gene and the first marker gene remain linked together, but neither the RecA-like protein gene nor the first marker gene remain linked to the integrated PEU;
      (iii) the PEU comprises a third marker gene, a eukaryotic promoter, at least one 5' vector-derived exon, and an intron or fragment thereof; wherein the 5' vector-derived exon is adjacent to the intron or fragment thereof and is operatively downstream from the eukaryotic promoter; wherein when the trappable eukaryotic gene comprises an exon with a 3' splice acceptor, the PEU can integrate into the BBPAC placing the exon of the trappable eukaryotic gene operatively downstream of the PEU; and
      (iv) wherein neither the host cell nor the BBPAC independently or in conjunction can support homologous recombination, without the conditional replication shuttle vector;
   (b) growing the host cell under conditions in which the conditional replication shuttle vector can replicate, the RecA-like gene can be expressed, and in which a cell that contains the first and second marker genes is selected for; and wherein a first homologous recombination event occurs between the recombination cassette and the BBPAC to form a co-integrate;

(c) growing the cell selected for in step (b) under conditions in which the conditional replication shuttle vector cannot replicate and in which a cell that contains the first and second marker proteins is selected for, whereby a cell containing the co-integrate between the recombination cassette and the BBPAC is selected for; and (d) growing the cell selected for in step (c) under conditions in which the conditional replication shuttle vector cannot replicate and in which a cell that contains the second marker gene is selected for; wherein a second homologous recombination event occurs between the conditional replication shuttle vector and the BBPAC; and wherein the PEU is placed into the BBPAC.

2. The method of claim 1 wherein the PEU does not contain an exon encoding a 3' polyadenylation sequence.

3. A method of isolating a cell that contains a BBPAC having a eukaryotic promoter exon/intron unit (PEU) and a trappable eukaryotic gene comprising growing the cell selected for in step (d) of claim 1 under conditions in which a cell that contains the second and third marker genes is selected for, while a cell that contains the first marker gene is selected against; wherein a cell containing a BBPAC having a eukaryotic promoter exon/intron unit (PEU) is isolated.

4. The method of claim 3 wherein the first marker gene is a tetracycline resistance gene that can be counter-selected against by growing the cell in the presence of fusaric acid.

5. The method of claim 1 wherein the PEU is a bi-directional eukaryotic promoter-exon/intron unit (BPEU).

6. The method of claim 1 wherein the conditional replication shuttle vector is a temperature sensitive shuttle vector (TSSV) having a temperature-sensitive origin of replication, wherein the TSSV replicates at a permissive temperature, but does not replicate at a non-permissive temperature.

7. The method of claim 1 wherein the BBPAC is a BAC.

8. The method of claim 1 wherein the PEU comprises two 5' vector-derived exons and one intron.

9. The method of claim 8 wherein the two 5' vector-derived exons consist of the first exon of beta-globin and a fusion exon containing the second exon of beta-globin fused to the HIV-tat exon; the intron is the HIV-tat intron; and wherein the fusion exon is adjacent to the HIV-tat intron.

10. A method of transcribing a trappable eukaryotic gene contained in a BBPAC in a eukaryotic cell comprising:

(a) isolating the BBPAC containing the trappable eukaryotic gene operably downstream of the PEU from the isolated cell of claim 3;

(b) transfecting the isolated BBPAC into a eukaryotic cell; and (c) culturing the eukaryotic cell; wherein when the PEU is operatively upstream to an exon of the trappable eukaryotic gene, the eukaryotic promoter of the PEU facilitates the transcription of the exon of the trappable eukaryotic gene into an MRNA; wherein the trappable eukaryotic gene is transcribed.

11. A method of determining the nucleotide sequence of a trappable eukaryotic gene contained in a BBPAC comprising:

(a) preparing a cognate cDNA of the mRNA of claim 10 as a template; and (b) determining the nucleotide sequence of the cognate cDNA; wherein the nucleotide sequence of the trappable eukaryotic gene contained in the BBPAC is determined.

12. The method of claim 11 wherein preparing the cognate cDNA is performed by PCR.

13. A method of placing a eukaryotic promoter exon/intron unit (PEU) into a BBPAC that contains a trappable eukaryotic gene comprising:

(a) introducing a shuttle vector into a host cell containing the BBPAC under conditions in which the shuttle vector can replicate and transform the host cell wherein:

(i) the BBPAC contains a trappable eukaryotic gene, BBPAC vector DNA, and a second marker gene;

(ii) the shuttle vector comprises a first marker gene which can be counter-selected against, the PEU, a mini-transposon containing a pair of inverted transposon ends, a nucleic acid encoding transposase, and an inducible promoter; wherein the expression of transposase is under the control of the inducible promoter; wherein the PEU is positioned in between the pair of inverted transposon ends; and the nucleic acid encoding transposase, the inducible promoter, and the first marker gene are positioned outside of the pair of inverted transposon ends; and (iii) the PEU comprises a third marker gene, a eukaryotic promoter, at least one 5' vector-derived exon, and an intron or fragment thereof; wherein a 5' vector-derived exon is adjacent to an intron or fragment thereof and is operatively downstream from the eukaryotic promoter; wherein when the trappable eukaryotic gene comprises an exon with a 3' splice acceptor, the PEU can integrate into the BBPAC and place the exon of the trappable eukaryotic gene operatively downstream of the PEU;

(b) growing the host cell under conditions in which the shuttle vector can replicate, and in which a cell that contains the first and second marker gene are selected for; and (c) inducing the inducible promoter of the cell selected for in step (b), wherein transposase is expressed; and wherein the PEU is placed into the BBPAC.

14. The method of claim 13 wherein the PEU does not contain an exon encoding a 3' polyadenylation sequence.

15. The method of claim 13 wherein the shuttle vector is a conditional replication shuttle vector.

16. A method of isolating a cell that contains a BBPAC having a eukaryotic promoter exon/intron unit (PEU) and a trappable eukaryotic gene comprising growing the cell selected for in step (c) of claim 15 under conditions in which the conditional replication shuttle vector cannot replicate, and in which a cell that contains the second and third marker genes are selected for, while a cell that contains the first marker gene is selected against; wherein a cell containing a BBPAC having a eukaryotic promoter exon/intron unit (PEU) is isolated.

17. The method of claim 16 wherein the first marker gene is a tetracycline resistance gene that can be counter-selected against by growing the cell in the presence of fusaric acid.

18. The method of claim 15 wherein the PEU is a bidirectional eukaryotic promoter-exon/intron unit (BPEU).

19. The method of claim 15 wherein the conditional replication shuttle vector is a temperature sensitive shuttle vector (TSSV) having a temperature-sensitive origin of replication, wherein the TSSV replicates at a permissive temperature, but does not replicate at a non-permissive temperature.

20. The method of claim 15 wherein the BBPAC is a BAC.

21. The method of claim 15 wherein the inducible promoter is the $\beta$-galactosidase promoter; wherein the host cell expresses lacI$^q$; and wherein said inducing of the inducible promoter comprises contacting the bacterial host cell with IPTG.

22. The method of claim 15 wherein the amount of IPTG used to contact the bacterial host is controlled so that the BBPAC receives only a single PEU.

23. The method of claim 15 wherein the inducible promoter is the β-galactosidase promoter; wherein the TSSV encodes lacI$^q$; and wherein said inducing of the inducible promoter comprises contacting the bacterial host cell with IPTG.

24. The method of claim 23 wherein the amount of IPTG used to contact the bacterial host is controlled so that the BBPAC receives only a single PEU.

25. A method of purifying a BBPAC having a eukaryotic promoter exon/intron unit (PEU) comprising
   (a) performing alkaline lysis of the isolated cell obtained from claim 16, wherein the BBPAC DNA is isolated;
   (b) electroporating the isolated BBPAC DNA into competent bacterial cells;
   (c) growing the competent bacterial cells under conditions in which the conditional replication shuttle vector cannot replicate and in which cells that contain the second and third marker genes are selected for; and
   (d) performing alkaline lysis of the bacterial cells selected for in step (c); wherein the BBPAC DNA is purified.

26. A method of transcribing a trappable eukaryotic gene contained in a BBPAC in a eukaryotic cell comprising:
   (a) transfecting the purified BBPAC from step (d) of claim 25 into a eukaryotic cell; and
   (b) culturing the eukaryotic cell; wherein when the BBPAC contains a eukaryotic promoter exon/intron unit (PEU) operatively upstream to an exon of the trappable eukaryotic gene, the eukaryotic promoter facilitates the transcription of the exon of the trappable eukaryotic gene into an mRNA; wherein the trappable eukaryotic gene is transcribed.

27. A method of determining the nucleotide sequence of a trappable eukaryotic gene contained in a BBPAC comprising:
   (a) preparing a cognate cDNA of the MRNA of claim 26 as a template; and
   (b) determining the nucleotide sequence of the cognate cDNA; wherein the nucleotide sequence of a trappable eukaryotic gene contained in the BBPAC is determined.

28. The method of claim 27 wherein preparing the cognate cDNA is performed by PCR.

29. The method of claim 15 further comprising mapping the insertion site of the PEU.

30. The method of claim 29 wherein the mapping is performed by a procedure selected from the group consisting of pulse field gel electrophoresis and Southern blots.

* * * * *